(12) United States Patent
Mordoh et al.

(10) Patent No.: US 8,501,168 B2
(45) Date of Patent: Aug. 6, 2013

(54) CELL LINES, COMPOSITIONS COMPRISING THEM FOR THE TREATMENT OF MELANOMAS, PROCEDURES TO PREPARE THE COMPOSITIONS, AND TREATMENT METHODS

(75) Inventors: José Mordoh, Buenos Aires (AR); María Marcela Barrio, Buenos Aires (AR); Erika María Von Euw, Buenos Aires (AR)

(73) Assignee: Consejo Nacional de Investigaciones Cientificas y Tecnicas (Conicet), Buenos Aires (AR)

( * ) Notice: Subject to any disclaimer, the term of this patent is extended or adjusted under 35 U.S.C. 154(b) by 439 days.

(21) Appl. No.: 12/450,721

(22) PCT Filed: Apr. 11, 2008

(86) PCT No.: PCT/IB2008/051385
§ 371 (c)(1),
(2), (4) Date: Jan. 6, 2010

(87) PCT Pub. No.: WO2008/126039
PCT Pub. Date: Oct. 23, 2008

(65) Prior Publication Data
US 2010/0183683 A1    Jul. 22, 2010

(30) Foreign Application Priority Data
Apr. 11, 2007 (AR) .............................. P20070101520

(51) Int. Cl.
*A61K 39/00* (2006.01)
*C12N 5/0784* (2010.01)
*C12N 5/09* (2010.01)

(52) U.S. Cl.
USPC ... 424/93.3; 424/93.7; 424/93.71; 424/277.1; 435/366; 435/372; 435/373; 435/374; 435/377

(58) Field of Classification Search
None
See application file for complete search history.

(56) References Cited

U.S. PATENT DOCUMENTS
6,497,876 B1 * 12/2002 Maraskovsky et al. .... 424/93.71

FOREIGN PATENT DOCUMENTS
| RU | 2004100550 A | | 6/2005 |
| RU | 2004137945 A | | 6/2006 |
| RU | 2283129 C1 | | 9/2006 |
| WO | WO01/29192 | * | 4/2001 |
| WO | WO03/020884 | * | 3/2003 |

OTHER PUBLICATIONS

Von Euw et al (Journal of Translational Medicine, Jan. 2008, vol. 6, pp. 1-14).*

* cited by examiner

*Primary Examiner* — Karen Canella
(74) *Attorney, Agent, or Firm* — Nath, Goldberg & Meyer; Tanya E. Harkins

(57) ABSTRACT

Cell lines, compositions comprising them for the treatment of melanomas, procedures to prepare the compositions, and treatment methods. More particularly, the invention relates to diverse human melanoma cell lines for the treatment of malignant diseases, wherein the cell lines are: (a) Mel-XY1 (deposited at German Collection of Microorganisms and Cell Cultures DSMZ under access number DSM ACC2830), (b) Mel-XY2 (deposited at German Collection of Microorganisms and Cell Cultures DSMZ under access number DSM ACC2831), (c) Mel-XY3 (deposited at German Collection of Microorganisms and Cell Cultures DSMZ under access number DSM ACC2832), (d) Mel-XX4 (deposited at German Collection of Microorganisms and Cell Cultures DSMZ under access number DSM ACC2829), or (e) sub-populations thereof. The cell lines may be irradiated, thus obtaining populations with apoptotic phenotype, and populations with necrotic phenotype of such lines. The compositions may comprise adjuvants and/or immuno-modifiers, and/or autologous dendritic cells.

45 Claims, 10 Drawing Sheets

SEQUENCE LISTING

```
<160> NUMBER OF SEQ ID NOS: 20

<210> SEQ ID NO 1
<211> LENGTH: 21
<212> TYPE: DNA
<213> ORGANISM: Artificial Sequence
<220> FEATURE:
<223> OTHER INFORMATION: GP100 5 prime -3 prime PRIMER

<400> SEQUENCE: 1
gcttggtgtc tcaaggcaac t                                        21

<210> SEQ ID NO 2
<211> LENGTH: 21
<212> TYPE: DNA
<213> ORGANISM: Artificial Sequence
<220> FEATURE:
<223> OTHER INFORMATION: anti-sense Gp100 primer

<400> SEQUENCE: 2
ctccaggtaa gtatgagtga c                                        21

<210> SEQ ID NO 3
<211> LENGTH: 26
<212> TYPE: DNA
<213> ORGANISM: Artificial Sequence
<220> FEATURE:
<223> OTHER INFORMATION: MART-1 5 prime-3 prime direction primer

<400> SEQUENCE: 3
caagatgcca agagaagatg ctcact                                   26

<210> SEQ ID NO 4
<211> LENGTH: 26
<212> TYPE: DNA
<213> ORGANISM: Artificial Sequence
<220> FEATURE:
```

<223> OTHER INFORMATION: MART-1 anti-sense primer

<400> SEQUENCE: 4
gcttgcattt ttcctacacc attcca                                              26

<210> SEQ ID NO 5
<211> LENGTH: 20
<212> TYPE: DNA
<213> ORGANISM: Artificial Sequence
<220> FEATURE:
<223> OTHER INFORMATION: 5 prime-3 prime sense tyrosinase primer

<400> SEQUENCE: 5
ttggcagatt gtctgtagcc                                                     20

<210> SEQ ID NO 6
<211> LENGTH: 20
<212> TYPE: DNA
<213> ORGANISM: Artificial Sequence
<220> FEATURE:
<223> OTHER INFORMATION: anti-sense tyirosinase primer

<400> SEQUENCE: 6
aggcattgtg catgctgctt                                                     20

<210> SEQ ID NO 7
<211> LENGTH: 20
<212> TYPE: DNA
<213> ORGANISM: Artificial Sequence
<220> FEATURE:
<223> OTHER INFORMATION: 5 prime-3 prime sense internal tyrosinase
      primer (nested DNA)

<400> SEQUENCE: 7
gtctttatgc aatggaacgc                                                     20

<210> SEQ ID NO 8
<211> LENGTH: 20
<212> TYPE: DNA
<213> ORGANISM: Artificial Sequence
<220> FEATURE:
<223> OTHER INFORMATION: anti-sense internal tyrosinase primer
      (nested PCR)

<400> SEQUENCE: 8
gctatcccag taagtggact                                                     20

<210> SEQ ID NO 9
<211> LENGTH: 21
<212> TYPE: DNA
<213> ORGANISM: Artificial Sequence
<220> FEATURE:
<223> OTHER INFORMATION: 5 prime-3 prime sense TRP-2 primer

<400> SEQUENCE: 9
gagtggtccc tacatcctac g                                                   21

<210> SEQ ID NO 10
<211> LENGTH: 21
<212> TYPE: DNA
<213> ORGANISM: Artificial Sequence
<220> FEATURE:
<223> OTHER INFORMATION: antisense TRP-2 primer

<400> SEQUENCE: 10
gcgtcctggt cctaataatg t                                                   21

```
<210> SEQ ID NO 11
<211> LENGTH: 19
<212> TYPE: DNA
<213> ORGANISM: Artificial Sequence
<220> FEATURE:
<223> OTHER INFORMATION: 5 prime-3 prime sense MAGE-1 primer

<400> SEQUENCE: 11
gagtcctcag ggagcctcc                                                19

<210> SEQ ID NO 12
<211> LENGTH: 20
<212> TYPE: DNA
<213> ORGANISM: Artificial Sequence
<220> FEATURE:
<223> OTHER INFORMATION: anti-sense MAGE-1 primer

<400> SEQUENCE: 12
ttgccgaaga tctcaggaaa                                               20

<210> SEQ ID NO 13
<211> LENGTH: 24
<212> TYPE: DNA
<213> ORGANISM: Artificial Sequence
<220> FEATURE:
<223> OTHER INFORMATION: 5 prime-3 prime sense NY-ESO-1 primer

<400> SEQUENCE: 13
agccgcctgc ttgagttcta cctc                                          24

<210> SEQ ID NO 14
<211> LENGTH: 21
<212> TYPE: DNA
<213> ORGANISM: Artificial Sequence
<220> FEATURE:
<223> OTHER INFORMATION: antisense NY-ESO-1 primer

<400> SEQUENCE: 14
agggaaagct gctggagaca g                                             21

<210> SEQ ID NO 15
<211> LENGTH: 21
<212> TYPE: DNA
<213> ORGANISM: Artificial Sequence
<220> FEATURE:
<223> OTHER INFORMATION: 5 prime-3 prime sense MDR-1 primer

<400> SEQUENCE: 15
tccaagaagc cctggacaaa g                                             21

<210> SEQ ID NO 16
<211> LENGTH: 25
<212> TYPE: DNA
<213> ORGANISM: Artificial Sequence
<220> FEATURE:
<223> OTHER INFORMATION: antisense MDR-1 primer

<400> SEQUENCE: 16
ttgatgatgt ctctcactct gttcc                                         25

<210> SEQ ID NO 17
<211> LENGTH: 27
<212> TYPE: DNA
<213> ORGANISM: Artificial Sequence
<220> FEATURE:
<223> OTHER INFORMATION: 5 prime-3 prime sense MIA primer
```

```
<400> SEQUENCE: 17
catgcatgcg gtcctatgcc caagctg                                              27

<210> SEQ ID NO 18
<211> LENGTH: 27
<212> TYPE: DNA
<213> ORGANISM: Artificial Sequence
<220> FEATURE:
<223> OTHER INFORMATION: anti-sense MIA primer

<400> SEQUENCE: 18
gataagcttt cactggcagt agaaatc                                              27

<210> SEQ ID NO 19
<211> LENGTH: 23
<212> TYPE: DNA
<213> ORGANISM: Artificial Sequence
<220> FEATURE:
<223> OTHER INFORMATION: 5 prime-3 prime sense beta-actin primer

<400> SEQUENCE: 19
atgtttgaga ccttcaacac ccc                                                  23

<210> SEQ ID NO 20
<211> LENGTH: 23
<212> TYPE: DNA
<213> ORGANISM: Artificial Sequence
<220> FEATURE:
<223> OTHER INFORMATION: anti-sense beta-actin primer

<400> SEQUENCE: 20
gccatctctt gctcgaagtc cag                                                  23
```

CELL LINES, COMPOSITIONS COMPRISING THEM FOR THE TREATMENT OF MELANOMAS, PROCEDURES TO PREPARE THE COMPOSITIONS, AND TREATMENT METHODS

This is a National Phase Application filed under 35 U.S.C. 371 as a national stage of PCT/IB2008/051385, filed 11 Apr. 2008 and claiming priority from AR application No. P20070101520, filed 11 Apr. 2007, the entire content of which is hereby incorporated.

TECHNICAL FIELD

The present invention relates to cell lines, compositions comprising them for treating melanomas, procedures for preparing compositions, and treatment methods. More particularly, the invention relates to diverse human melanoma cell lines for treatment of malignant diseases, where the cell lines are: (a) Mel-XY1 (deposited at German Collection of Microorganisms and Cell Cultures DSMZ—Deutsche Sammlung von Mikroorganismen und Zellkulturen GmbH, Inhoffenstraβe 7 B 38124 Braunschweig, Germany on Mar. 23, 2007 under access number DSM ACC2830), (b) Mel-XY2 (deposited at German Collection of Microorganisms and Cell Cultures DSMZ—Deutsche Sammlung von Mikroorganismen und Zellkulturen GmbH, Inhoffenstraβe 7 B 38124 Braunschweig, Germany on Mar. 23, 2007 under access number DSM ACC2831), (c) Mel-XY3 (deposited at German Collection of Microorganisms and Cell Cultures DSMZ—Deutsche Sammlung von Mikroorganismen und Zellkulturen GmbH, Inhoffenstraβe 7 B 38124 Braunschweig, Germany on Mar. 23, 2007 under access number DSM ACC2832), (d) Mel-XX4 (deposited at German Collection of Microorganisms and Cell Cultures DSMZ—Deutsche Sammlung von Mikroorganismen und Zellkulturen GmbH, Inhoffenstraβe 7 B 38124 Braunschweig, Germany on Mar. 23, 2007 under access number DSM ACC2829) or (e) subpopulations thereof. Cell lines may be irradiated, thus obtaining populations with apoptotic phenotype, and populations with necrotic phenotype of such lines. The compositions may comprise adjuvants, and/or immuno-modifiers, and/or autologous dendritic cells.

BACKGROUND OF THE INVENTION

Currently, many efforts are done, and many resources are used to research on the area of cancer immunotherapy. Important existing evidences indicate a central role of T lymphocytes in cancer effective immune responses (Oliver R T, Nouri A M. T; Cancer Surv 1992; 13:173-204). To such purpose, treatments with allogenic cells alone, with adjuvants, or in combination with some cytokines have been used.

On the other hand, it is known that dendritic cells (DC) are antigen presenting cells that may initiate a T cell response, due to their extraordinary ability to stimulate naïve T lymphocytes (Schuler G, Steinman R M. J. Exp. Med. 1997; 186:1183-7, and Banchereau J, Steinman R M. Nature 1998; 392:245-52).

Several authors have shown in mouse models, and in humans that DC incorporate apoptotic cells, and thus the antigens for the generation of Class I HLA complexes/peptides are presented, allowing the induction of cytotoxic T lymphocytes (Albert M L, Pearce S F, Francisco L M, Sauter B, Roy P, Silverstein R L, Bhardwaj N. J Exp Med. 1998, 188: 1359-1368; Chen Z, Moyana T, Saxena A, Warrington R, Jia Z, Xiang J. Int J. Cancer. 2001, 93: 539-548 and Shaif-Muthana M, McIntyre C, Sisley K, Rennie I, Murray A. Cancer Res. 2000, 60: 6441-6447). For this process it is fundamental that the apoptotic cells induce maturity of the dendritic cells (DC), however, many authors have informed that human apoptotic cells do not mature DC, or induce loss of maturity of such DC (Pietra G, Mortarini R, Parmiani G, Anichini A. Cancer Res 2001, 61: 8218-8226; Labarriere N, Bretaudeau L, Gervois N, Bodinier M, Bougras G, Diez E, Lang F, Gregoire M, Jotereau F. Int J Cancer 2002, 101: 280-286 and Demaria S, Santori F R, Ng B, Liebes L, Formenti S C, Vukmanovic S. J Leukoc Biol. 2005, 77: 361-368).

U.S. Pat. No. 6,187,306 by Pardoll et al. discloses a method of treating and protecting against melanoma, which comprises the use of at least one or more allogenic cell lines expressing melanoma immunodominant antigens, wherein the cell line has been modified in such a way that it expresses cytokines, and administering such transformed line to a patient carrying melanoma, or at risk of getting the disease. Although the importance of the cell line or the cell lines used, which expresses most of the immunodominant antigens, a new cell line or a combination of cell lines expressing most of such antigens have not been disclosed. The invention comprises essentially transformed cell lines expressing cytokines such as GM-CSF.

U.S. Pat. No. 5,882,654, and U.S. Pat. No. 5,840,317 disclose irradiated melanoma cell lines used as allogenic vaccines. The disclosed treatment reaches levels of NED patients below 50% (16/37), and shows an effective humoral-type anti-tumor activity.

US patent 2006/0034811 by Wallack et al. discloses vaccines comprising antigen presenting cells charged with lysed or ruptured tumor cells including cytosol and membranes. Tumor cells may be cells from the patient, cell lines, or cells infected with the recombinant vaccinia virus codifying IL-2.

US patent 2006/0140983 by Palucka et al. discloses a composition inducing immunity in cancer patients which comprises the isolation and purification of antigen presenting cells primed for exposition with one or more heat-shock proteins, and dead tumor cells. Antigen presenting cells are dendritic cells, and tumor cells may be syngenic or allogenic cells, for example cell lines. This document discloses the need of incorporating heat-shock proteins by rupture through heating of tumor cells. The shown assays do not necessarily disclose that the composition have immunity-inducing activity in melanoma patients.

U.S. Pat. No. 6,602,709 by Albert et al., discloses the use of apoptotic cells to present antigens to dendritic cells for T cell induction. The method is useful to induce antigen-specific cytotoxic T lymphocyte helper cells. Dendritic cells are primed by apoptotic cells or fragments thereof, and are capable of processing and present processed antigens, and induce the activity of cytotoxic T lymphocytes, which may be used as therapeutic vaccines.

BRIEF DESCRIPTION OF THE INVENTION

In one aspect of the present invention several human melanoma cell lines for the treatment of malignant diseases are provided, wherein the cell lines are (a) Mel-XY1 (deposited at German Collection of Microorganisms and Cell Cultures DSMZ under access number DSM ACC2830), (b) Mel-XY2 (deposited at German Collection of Microorganisms and Cell Cultures DSMZ under access number DSM ACC2831), (c) Mel-XY3 (deposited at German Collection of Microorganisms and Cell Cultures DSMZ under access number DSM ACC2832), (d) Mel-XX4 (deposited at German Collection of Microorganisms and Cell Cultures DSMZ under access number DSM ACC2829), or (e) sub-populations thereof. The cell lines may further be irradiated in order to obtain populations with apoptopic phenotype, and populations with such lines necrotic phenotype.

In another aspect of the present invention, a composition for the treatment of melanoma is provided, wherein such composition comprises al least one allogenioc melanoma cell line, for example (a) Mel-XY1 (deposited at German Collection of Microorganisms and Cell Cultures DSMZ under access number DSM ACC2830), (b) Mel-XY2 (deposited at German Collection of Microorganisms and Cell Cultures DSMZ under access number DSM ACC2831), (c) Mel-XY3 (deposited at German Collection of Microorganisms and Cell Cultures DSMZ under access number DSM ACC2832), (d) Mel-XX4 (deposited at German Collection of Microorganisms and Cell Cultures DSMZ under access number DSM ACC2829), or combinations thereof, wherein such cell lines are incapable of proliferate. The composition may also comprise excipients, adjuvants such as BCG, and immunomodulators such as GM-CSF, or IFNα. In a preferred embodiment, the composition comprises combinations of the four allogenic melanoma cell lines (a) Mel-XY1 (deposited at German Collection of Microorganisms and Cell Cultures DSMZ under access number DSM ACC2830), (b) Mel-XY2 (deposited at German Collection of Microorganisms and Cell Cultures DSMZ under access number DSM ACC2831), (c) Mel-XY3 (deposited at German Collection of Microorganisms and Cell Cultures DSMZ under access number DSM ACC2832) and (d) Mel-XX4 (deposited at German Collection of Microorganisms and Cell Cultures DSMZ under access number DSM ACC2829), where such cell lines have been irradiated and are incapable of proliferate. In another preferred embodiment, the composition of the invention comprising combinations of the three allogenic melanoma cell lines (a) Mel-XY1 (deposited at German Collection of Microorganisms and Cell Cultures DSMZ under access number DSM ACC2830), (b) Mel-XY2 (deposited at German Collection of Microorganisms and Cell Cultures DSMZ under access number DSM ACC2831), and (c) Mel-XY3 (deposited at German Collection of Microorganisms and Cell Cultures DSMZ under access number DSM ACC2832), where such cell lines have been irradiated and are incapable of proliferate.

In another aspect of the present invention, a composition for adjuvant treatment of melanoma is provided, wherein such composition comprises at least one allogenic melanoma cell line, for example (a) Mel-XY1 (deposited at German Collection of Microorganisms and Cell Cultures DSMZ under access number DSM ACC2830), (b) Mel-XY2 (deposited at German Collection of Microorganisms and Cell Cultures DSMZ under access number DSM ACC2831), (c) Mel-XY3 (deposited at German Collection of Microorganisms and Cell Cultures DSMZ under access number DSM ACC2832), (d) Mel-XX4 (deposited at German Collection of Microorganisms and Cell Cultures DSMZ under access number DSM ACC2829), and combinations thereof, and where such cell lines have been irradiated and are incapable of proliferate. The composition may also comprise excipients, adjuvants such as BCG, and immunomodificadores such as GM-CSF and/or IFNα. In one preferred embodiment the composition of the invention comprises a combination of the allogenic melanoma cell lines (a) Mel-XY1 (deposited at German Collection of Microorganisms and Cell Cultures DSMZ under access number DSM ACC2830), (b) Mel-XY2 (deposited at German Collection of Microorganisms and Cell Cultures DSMZ under access number DSM ACC2831), (c) Mel-XY3 (deposited at German Collection of Microorganisms and Cell Cultures DSMZ under access number DSM ACC2832), or (d) Mel-XX4 (deposited at German Collection of Microorganisms and Cell Cultures DSMZ under access number DSM ACC2829), where such cell lines have been irradiated and are incapable of proliferate. In another preferred embodiment, the composition of the invention comprises a combination of the allogenic melanoma cell lines (a) Mel-XY1 (deposited at German Collection of Microorganisms and Cell Cultures DSMZ under access number DSM ACC2830), (b) Mel-XY2 (deposited at German Collection of Microorganisms and Cell Cultures DSMZ under access number DSM ACC2831), or (c) Mel-XY3 (deposited at German Collection of Microorganisms and Cell Cultures DSMZ under access number DSM ACC2832), where such cell lines have been irradiated and are incapable of proliferate.

In another aspect of the present invention, a composition is provided for the treatment of human melanomas comprising mature autologous dendritic cells, autologous dendritic cells charged with cells with at least a allogenic human melanoma cell line, apoptotic cells of such at least one heterologous human melanoma cell line of such at least one heterologous human melanoma cell line. The human melanoma cell line is one or more of the following lines: (a) Mel-XY1 (deposited at German Collection of Microorganisms and Cell Cultures DSMZ under access number DSM ACC2830), (b) Mel-XY2 (deposited at German Collection of Microorganisms and Cell Cultures DSMZ under access number DSM ACC2831), (c) Mel-XY3 (deposited at German Collection of Microorganisms and Cell Cultures DSMZ under access number DSM ACC2832), (d) Mel-XX4 (deposited at German Collection of Microorganisms and Cell Cultures DSMZ under access number DSM ACC2829), or (e) subpopulations thereof.

In another aspect of the invention, a composition for adjuvant treatment of human melanoma is provided, comprising mature dendritic cells, dendritic cells charged with cells of at least one allogenic human melanoma cell line, apoptotic cells of one heterologous human melanoma cell line and necrotic cells of one heterologous human melanoma cell line. The melanoma cell line is one or more of the following cell lines: (a) Mel-XY1 (deposited at German Collection of Microorganisms and Cell Cultures DSMZ under access number DSM ACC2830), (b) Mel-XY2 (deposited at German Collection of Microorganisms and Cell Cultures DSMZ under access number DSM ACC2831), (c) Mel-XY3 (deposited at German Collection of Microorganisms and Cell Cultures DSMZ under access number DSM ACC2832), (d) Mel-XX4 (deposited at German Collection of Microorganisms and Cell Cultures DSMZ under access number DSM ACC2829), or subpopulations thereof.

In another aspect of the present invention, a procedure for preparing the composition is provided, wherein such procedure is carried out in the following stages:
  a) thawing and culturing cell lines (a) Mel-XY1 (deposited at German Collection of Microorganisms and Cell Cultures DSMZ under access number DSM ACC2830), (b) Mel-XY2 (deposited at German Collection of Microorganisms and Cell Cultures DSMZ under access number DSM ACC2831), and (c) Mel-XY3 (deposited at German Collection of Microorganisms and Cell Cultures DSMZ under access number DSM ACC2832);
  b) blending such three cell lines;
  c) irradiating such three cell lines;
  d) adding adjuvants and excipients to the cell line mixtures. The procedure may also comprise in stage a) adding cell line Mel-XX4 (deposited at German Collection of Microorganisms and Cell Cultures DSMZ under access number DSM ACC2829).

In another object of the present invention, a procedure for preparing the composition is provided, which comprises the stages of:

a) thawing and culturing cell lines (a) Mel-XY1 (deposited at German Collection of Microorganisms and Cell Cultures DSMZ under access number DSM ACC2830), (b) Mel-XY2 (deposited at German Collection of Microorganisms and Cell Cultures DSMZ under access number DSM ACC2831), (c) Mel-XY3 (deposited at German Collection of Microorganisms and Cell Cultures DSMZ under access number DSM ACC2832), and Mel-XX4 (deposited at German Collection of Microorganisms and Cell Cultures DSMZ under access number DSM ACC2829);
b) blending such cell lines;
c) irradiating such cell lines;
d) obtaining autologous dendritic cells; and
e) co-culturing for some time the autologous dendritic cells with the irradiated cell lines of stage c).

In another aspect of the present invention, a method to induce an anti-tumor immune response in patients carrying a melanoma is provided, which comprises administering to a patient in need thereof an affective amount of a combination of cell lines (a) Mel-XY1 (deposited at German Collection of Microorganisms and Cell Cultures DSMZ under access number DSM ACC2830), (b) Mel-XY2 (deposited at German Collection of Microorganisms and Cell Cultures DSMZ under access number DSM ACC2831), and (c) Mel-XY3 (deposited at German Collection of Microorganisms and Cell Cultures DSMZ under access number DSM ACC2832), where such cell lines are incapable of proliferate. The administration may be done together adjuvants and/or immunomodulators.

In another aspect of the present invention, a method of inducing an anti-tumor immune response in patients carrying a melanoma is provided, which comprises administering to a patient in need thereof an effective amount of a combination of cell lines (a) Mel-XY1 (deposited at German Collection of Microorganisms and Cell Cultures DSMZ under access number DSM ACC2830), (b) Mel-XY2 (deposited at German Collection of Microorganisms and Cell Cultures DSMZ under access number DSM ACC2831), (c) Mel-XY3 (deposited at German Collection of Microorganisms and Cell Cultures DSMZ under access number DSM ACC2832), and (d) Mel-XX4 (deposited at German Collection of Microorganisms and Cell Cultures DSMZ under access number DSM ACC2829), where such cell lines are incapable of proliferating.

In another aspect of the present invention, a method of inducing an anti-tumor immune response in patients carrying a melanoma is provided, which comprises administering to a patient in need thereof an effective amount of a co-culture from between 6 and 72 hours of autologous dendritic cells, and a combination of cell lines (a) Mel-XY1 (deposited at German Collection of Microorganisms and Cell Cultures DSMZ under access number DSM ACC2830), (b) Mel-XY2 (deposited at German Collection of Microorganisms and Cell Cultures DSMZ under access number DSM ACC2831), (c) Mel-XY3 (deposited at German Collection of Microorganisms and Cell Cultures DSMZ under access number DSM ACC2832), and (d) Mel-XX4 (deposited at German Collection of Microorganisms and Cell Cultures DSMZ under access number DSM ACC2829), where such cell lines are incapable of proliferating.

DETAILED DESCRIPTION OF THE INVENTION

Figure 1:
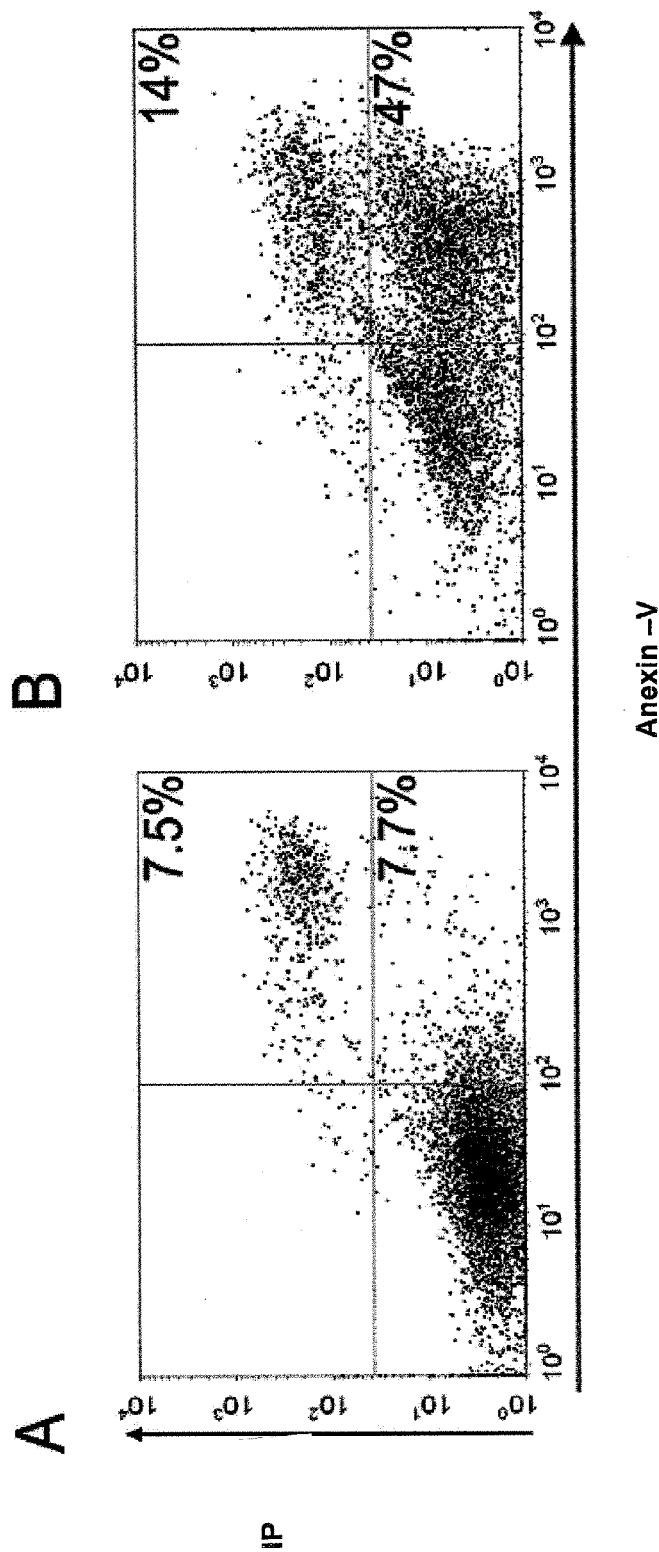
FIG. 1 shows a representative example of the results of Gamma irradiation of the mixture of cell lines of la invention in reference to apoptosis induction and necrosis (Apo-Nec cells). Panel A shows non-irradiated cells, and panel B shows the cells after Gamma irradiation 70Gy, and stained with Anexin V-FITC and IP (propidium iodide). Early apoptotic cells are defined as Anexin V-FITC$^+$/IP$^-$, while necrotic cells were doubly positive.

As regards this application, the terms "combination", and "mixture" are interchangeable.

Where in the present invention reference is made to compositions which modify the immune system in mammals it must be understand that these compositions are also known by skilled in the art as vaccine compositions, cell based vaccines, or simply vaccines.

The four cell lines of the invention were deposited according the Budapest Treaty with the German Collection of Microorganisms and Cell Cultures DSMZ en Mar. 23, 2007 under the following access numbers: Mel-XY1 DSM ACC2830 cell line, Mel XY2 DSM ACC2831 line, Mel XY3 DSM ACC2832 line, and Mel XX4 DSM ACC2829 line.

The results of cell line characterization assays are shown in the following Table:

TABLE 1

HUMAN MELANOMA TUMOR CELL MARKERS OF THE INVENTION

| MARKER | XY1 | XY2 | XY3 | XX4 |
|---|---|---|---|---|
| Gp100 (HMB45) | ND | ND | + | + |
| Gp100 (PCR) | + | + | + | + |
| Tyrosinase (PCR) | + | + | + | + |
| MART-1 (PCR) | + | − | + | − |
| MAGE 1 (PCR) | ND | − | + | + |
| S100 | + | + | + | + |
| Vimentin | ND | + | + | + |
| CEA | ND | + | + | ND |
| GD2 | + | + | + | + |
| GD3 | + | + | + | + |
| P53 | + | + | + | + |
| MIA | + | + | + | + |
| MCP-1 | − | + | + | + |
| TRP-2 | + | + | ND | + |
| MDR1 | − | ND | − | − |
| HLA class I | A02/23 B18/B37 | A30/33 B18/B65 | A02/ A23 B18 | A24(9)/A33(19) B18/B65 (14) |
| HLA class II | DR7/DR11 DR52/DR53 | DR1/DR1 | DR11 DR13 DR52 | DR1/DR11 |
| Tumorigenicity in nude mice | + | + | + | + |
| Growth in soft agar colonies | ++ | ++ | ++++ | ++ |

From the MEL-XY1 cell line characterization appears that cells grow as a heterogeneous amelanotic cell monolayer in size and shape, where most are cubic or elongated in shape, and without extensions. They are slightly melanotic at high density. MEL-XY1 cells form great amount of colonies in semi-solid agar. MEL-XY1 cells are tumorigenic in athymic mice (nude), and do not generate metastasis.

From the MEL-XY2 cell line characterization appears that cells grow as a heterogeneous amelanotic cell monolayer in size. The cells are small in size and in less number, multi-nucleated and with prominent nucleoli. Cells with characteristic dendritic extensions in melanoma are also seen. By growing at high density, they may pile up and develop micro-tumors. MEL-XY2 cells are tumorigenic in athymic mice (nude), and do not generate metastases.

From the MEL-XY3 cell line characterization appears that cells grow in mono-layer. Cells are uniform, small, and partly rounded. By growing at high density, they may pile up and develop micro-tumors. MEL-XY3 cells form numerous colonies in semi-solid agar. MEL-XY3 cells are tumorigenic in athymic mice (nude), and do not generate metastases.

From the Mel-XX4 cell line characterization appears that such line grows in spindle-formed mono-layer at high density. At low density, it shows dendritic projections similar to melanocytes. Cells are melanotic, and some of them have multiple nuclei with prominent nucleolus. Population duplication time is of 172-173 hours, and they form colonies in soft agar assays.

When Mel-XX4 cell line of the invention was transplanted to nude mice (immuno-depressed) tumor cell lines were generated in vivo. Serial passages from the initial tumors demonstrated that 100% of transplanted animals developed tumors during the first month. Tumor growth was slowly, and at 84 days reached an average value of $372\pm63$ mm$^3$. Cell line Mel-XX4 of the invention is tumorigenic when injecting subcutaneously an amount of $3\times10^6$ cells.

From the analysis of modal chromosome number, the following appears: MEL-XY1 line of the invention shows a dispersion in chromosomal count (between 105 and 110), and thus a clear modal number did not stand out (male). MEL-XY2 line of the invention shows a bimodal tendency with chromosome numbers 89 and 91 (male). MEL-XY3 cell line of the present invention shows a modal number of (male). Most frequent number alterations were chromosome absence on pairs 2 and 6, and extra chromosomes on pairs 20 and 22. MEL-XY4 cell line of the invention shows a modal number of 57-58 (female sex).

Gamma radiation inducing apoptosis in the cell lines of the invention was studied. The application of 50 Gy radiation was enough to totally suppress clonogenic capacity in soft agar for each cell line of the invention. No significant differences were observed in the apoptosis/necrosis induction degree when cells were irradiated with 70, or 100 Gy. FIG. 1A showed that non-irradiated melanoma cells contained between 6-9% early apoptotic cells characterized by Anexin-V$^+$/IP$^-$ coloration (bottom right hand panel). After radiation at 70 Gy and 72 hr culture, 45-53% of early apoptotic cells were obtained (see FIG. 1B, bottom right hand panel). Anexin-V and IP stained necrotic cells increased from 7.5% in non-irradiated cells to about 15% in irradiated cells (top left hand panels). Thus, in reference to the present patent application, irradiated melanoma cells of the invention are called Apo-Nec cells, and the composition comprising one or more of any of the Apo-Nec cell lines (Mel-XY1, Mel-XY2, Mel-XY3 and/or Mel-XX4) is known as Apo-Nec composition.

Cell irradiation allowed to obtain cells incapable of proliferate, useful for the manufacture of compositions such as Apo-Nec composition of the invention. It shall be evident for a skilled in the art that the Apo-Nec composition of the invention may comprise any of the lines of the invention or different combinations thereof. In a preferred embodiment, composition Apo-Nec of the invention comprises a mixture or combination of Mel-XY1, Mel-XY2, and Mel-XY3 cell lines. In another preferred embodiment, composition Apo-Nec of the invention comprises a mixture, or combination of Mel-XY1, Mel-XY2, Mel-XY3, and Mel-XX4 cell lines. The mixture of the preferred Apo-Nec cell linea of the invention provides a combination of multiple antigens inducing an excellent anti-tumor immune response.

Figure 8:
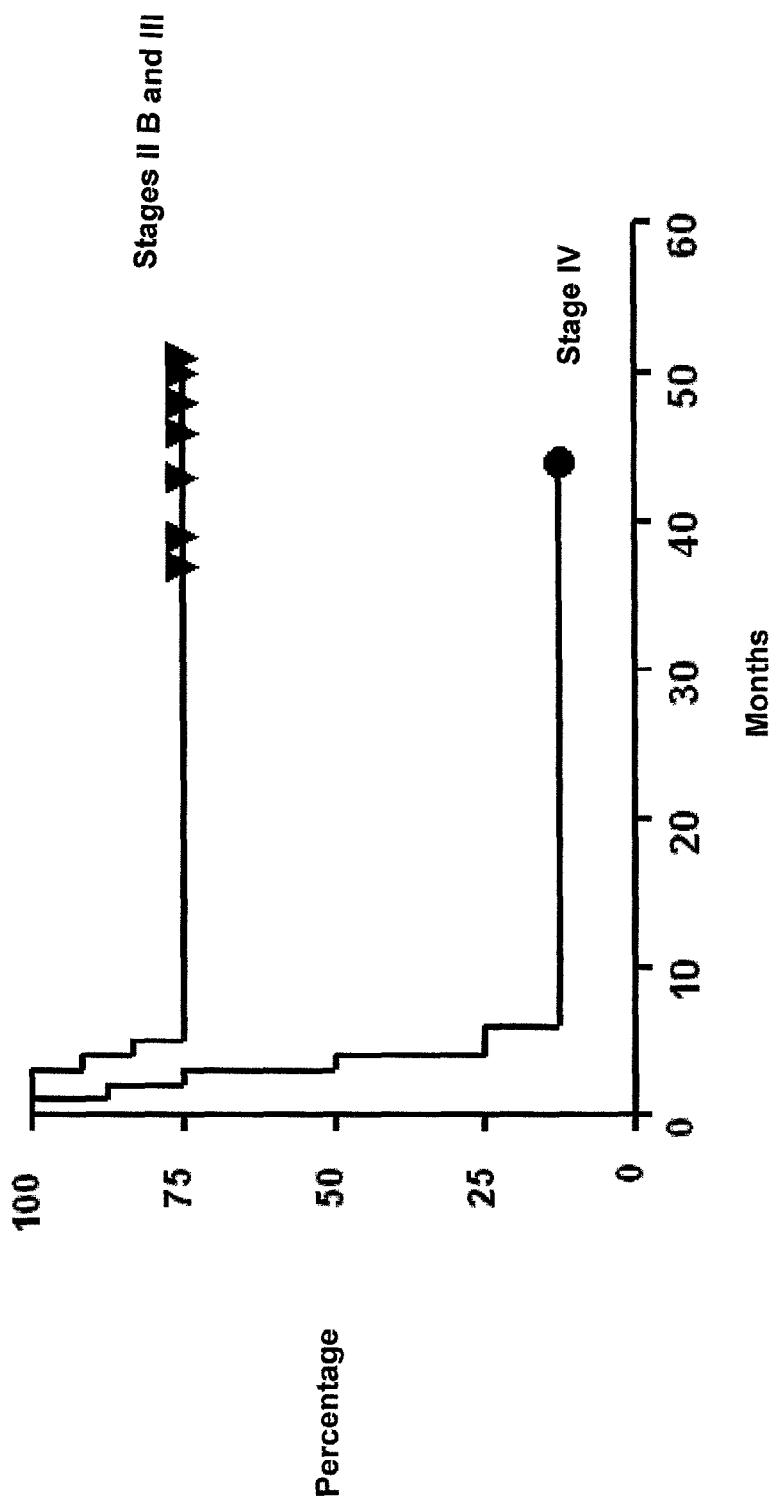
FIG. 8 shows a Kaplan-Meier graph of patients treated with the Apo-Nec composition of the invention.

Surprisingly, the combination of tumor antigens presented by the mixture of the four Apo-Nec cell lines of the invention induce a specific T cell immune response against the tumor, and allows to obtain more than 80% of patients free of disease, when treated with Apo-Nec composition of the invention (see FIG. 8).

The lines of the invention were also used to prepare de composition of the invention known as DC/Apo-Nec, which comprises at least one of the cell lines of the invention and autologous dendritic cells.

In a preferred embodiment, the cell lines are different combinations of lines Mel-XY1, Mel-XY2, Mel-XY3, and Mel-XX4. As an example, and without limitation, the combination may comprise a mixture of cell lines Mel-XY1, and Mel-XY2, or a mixture of lines Mel-XY1, Mel-XX4. In a preferred embodiment, the combination of cell lines comprises a mixture of cell lines Mel-XY1, Mel-XY2, Mel-XY3, and Mel-XX4; therefore, the four cells are present.

In a preferred embodiment, composition DC/Apo-Nec of the invention comprises a combination of irradiated cell lines Mel-XY1, Mel-XY2, Mel-XY3, Mel-XX4, and autologous dendritic cells.

The particular combination of the four cell lines of the invention provides a unique source of native antigens to charge dendritic cells, additionally providing antigens of clonogenic cells. It must be taken into account that the combination of the four irradiated cell lines of the invention not only provides a particular combination of native antigens, but also comprises a particular combination of cell population, wherein about 50% of apoptotic cells, and about 15% of necrotic cells are present. This combination of populations induces maturity of DC.

Stage I study with composition DC/Apo-Nec of the invention was performed in 16 melanoma patients which characteristics are shown in Table 2 received radiotherapy in the armpit area after surgery, due to rupture of the lymphatic node capsule. Cohorts of four patients were treated and washed with 5, 10, 15, or $20 \times 10^6$ dendritic cells (CDs) co-cultured with Apo-Nec cells (composition DC/Apo-Nec of the invention). Every patient received each two weeks a dose of the composition DC/Apo-Nec (0.3 ml) without adjuvants. Patient #7 was eliminated from de protocol after a second application due to a rapid progression of the disease after a sport trauma on the right thigh, and a non-controlled infection; this patient was not replaced.

Immature dendritic cells (DCin) showed the following pattern: $95.1 \pm 3.6\%$ were CD14$^-$/CD11c+, and $70 \pm 6\%$ were CD1a$^+$. Purity was esteemed in about 60%.

About $3 \times 10^6$ DCs were obtained from $1 \times 10^8$ PBMC sown in medium free from serum.

When DCin obtained from patients, and the cells comprised in the composition DC/Apo-Nec of the invention were characterized it was found that $42.3\% \pm 13.7$ of Dcin cells from patients (n=15) were able of fagociting Apo-Nec cells of the invention. Phagocytosis of Apo-Nec cells was assessed by electronic microscopy, observing whole Apo-Nec cells or parts of them within DCs in vacuoles.

The ability of the Apo-Nec cells of the invention to affect the maturation process of the monocyte derivative DC cells

TABLE 2 characteristics of patients

| Patient | Sex | Age | Clinical stage | Mts | PBMC ($\times 10^9$ cells) | Dose of DC/Apo-Nec ($\times 10^6$ cells) | Dose | Clinical evolution (30/3/07) | DTH score |
|---|---|---|---|---|---|---|---|---|---|
| 1 | F | 42 | IV | LN | 3.5 | 5 | 4 | P (8 m) | 4 |
| 2 | F | 57 | III | ND | 3.6 | 5 | 4 | NED (54 m+) | 8 |
| 3 | M | 32 | III | ND | 3.3 | 5 | 4 | NED (35 m+) | 14.25 |
| 4 | F | 17 | III | ND | 4.4 | 5 | 4 | NED (45 m+) | 9.5 |
| 5 | M | 56 | IV | L | 5 | 10 | 4 | P (4 m) | 4 |
| 6 | M | 60 | III | ND | 1.5 | 3 | 4 | NED (37 m+) | 4.5 |
| 7 | M | 27 | IV | SC | 4.2 | 10 | 2 | WP (1 m) | ND |
| 8 | M | 26 | III | ND | 3.6 | 10 | 4 | P (7 m) | 10.5 |
| 9 | F | 42 | III | ND | 7.5 | 15 | 4 | NED (71 m+) | 5.6 |
| 10 | M | 34 | IV | LN | 6.2 | 15 | 4 | P (11 m) | 5.5 |
| 11 | M | 44 | IV | L | 4.7 | 15 | 4 | P (4 m) | 10 |
| 12 | M | 56 | III | ND | 8 | 15 | 4 | NED (25 m+) | 4.5 |
| 13 | M | 47 | IIC | ND | 9.3 | 20 | 4 | NED (26 m+) | 6.5 |
| 14 | M | 30 | III | ND | 7.5 | 20 | 4 | NED (39 m+) | 7.25 |
| 15 | M | 52 | IV | LN | 6 | 20 | 4 | P (10 m) | 3.75 |
| 16 | F | 57 | IV | SC | 8.2 | 20 | 4 | P (6 m) | 5.25 |

ND: Non detectable;
SC: subcutaneous;
L: lung
LN: lymph node

Average age was 42 years (ranging from 17 to 60 years). Five women and eleven men were treated. One of the patients had stage IIC AJCC melanoma, eight had stage III melanoma, and seven had stage IV melanoma. Patients #5 and #11 had been submitted to lung metastases surgery; patient #16 had subcutaneous metastases, and patients #1, #10, and #15 had was examined trough measurements of specific DC cell markers by flow cytometry (FACS) (FACSCalibur, BD Biosciences, San Jose, Calif.). Phagocytosis of the Apo-Nec cells of the invention resulted in a DC cell mature phenotype compared to controls incubated with LPS. DC cell maturity was evidenced by the increase of CD83, CD80, CD86, HLA class I, and II and CD40 expression. After phagocytosis, a 75.2%±16 reduction in endocytosis FITC-Dx was found, compared to DCin.

The chemokine receptor (C-C motif) receptor 7 (CCR7) increased its expression in DCs after phagocytosis of Apo-Nec cells of the invention in all patients, and this was related to CD cell migration in vitro towards MIP-3β. DCin cells (9.6% CCR7+, MFI: 23.3) migrated towards MIP-1α but not towards MIP-3β; in contrast, DC/Apo-Nec cells (81.8% CCR7+, MFI: 41.2) clearly migrated towards MIP-3β, and not towards MIP-1α.

Except patient #6, which showed low PBMC yield, and thus the $10 \times 10^6$ DC/Apo-Nec cell dose could not be obtained, and doses of $3 \times 10^6$ cells per application had to be administered, all remaining patients received the expected dosage of the DC/Apo-Nec composition of the invention cohort 1: $5 \times 10^6$, cohort 2: $10 \times 10^6$, cohort 3: $15 \times 10^6$, and cohort 4: $20 \times 10^6$. The DC/Apo-Nec composition of the invention was well tolerated, and mean toxicity cases found were always of Degree 1. Weak local reactions and DTH were found in the application sites, consisting in erythema, and papule. None of the patients developed autoimmune disease manifestations (Table 3).

TABLE 3

Toxicity associated to application of the DC/Apo-Nec composition of the invention

| Symptoms | Composition $5 \times 10^6$ | Composition $10 \times 10^6$ | Composition $15 \times 10^6$ | Composition $20 \times 10^6$ |
|---|---|---|---|---|
| Fatigue | 1/4 | 1/3 | 0/4 | 0/4 |
| Headache | 1/4 | 0/3 | 0/4 | 0/4 |
| Chills | 1/4 | 0/3 | 0/4 | 0/4 |
| Abdominal cramps | 0/4 | 0/3 | 0/4 | 1/4 |
| Local reaction | 4/4 | 3/3 | 4/4 | 4/4 |
| Asthenia | 0/4 | 1/3 | 0/4 | 0/4 |
| Nausea | 0/4 | 0/3 | 0/4 | 1/4 |
| Abdominal pain | 0/4 | 0/3 | 0/4 | 1/4 |
| Vomiting | 0/4 | 0/3 | 0/4 | 1/4 |
| Anorexia | 0/4 | 1/3 | 0/4 | 0/4 |
| Diarrhea | 0/4 | 0/3 | 0/4 | 1/4 |
| Myalgia | 1/4 | 0/3 | 1/4 | 0/4 |

Figure 2:
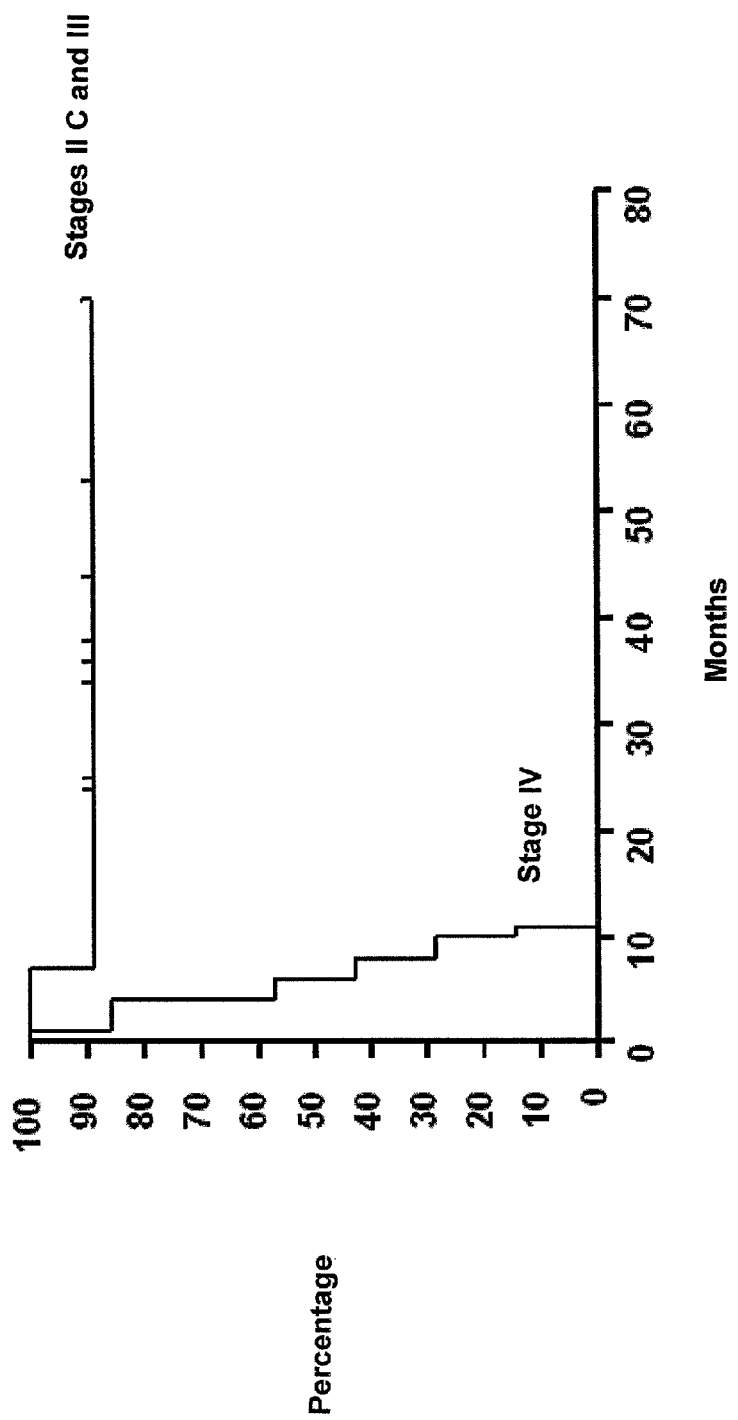
FIG. 2 shows a Kaplan Meier graph of patients treated with the composition of the invention DC/Apo-Nec.

After a mean follow-up of 41.5 months post-surgery (between 25 and 71 months), stage IIC patients showed no evidences of disease (NED); 7/8 (87.5%) of stage III patients were NED, and 7/7 of stage patients IV showed progression of the disease (see FIG. 2).

DTH reactions were assessed for each application to heterologous cells Apo-Nec of the invention and the intensity of the reaction was assessed, with the DTH score as described in the examples. Only 6/15 patients showed a slight DTH reaction before application against Apo-Nec cells of the invention. DTH assays disclosed that the application of Apo-Nec cells induce a specific reactivity in all patients, since the DTH score was significantly higher after the application of the second dose of the DC/Apo-Nec composition, compared to base reactions observed after the first application (Mann Whithney test P=0.029, n=15). DTH scores were higher in the NED patients than in those experiencing progression of the disease (P=0.28, Mann Wilcoxon Rank Sum test).

The increase of the amount of DC/Apo-Nec cells per application did not significantly increase DTH score.

No humoral response against living melanoma cells comprised in the composition of the invention was observed before and after the application, assessed through FACS analysis. Presence of reactive antibodies against Apo-Nec cells was also assessed in serum pre and post application, by the Western blot technique. In four patients (#3, #4, # and #16) only a tenuous band of melanoma protein (>200 kDa) was observed and detected in post-application serum, and which was not recognized in the breast cancer cell extracts used as non-specific control.

Figure 3:
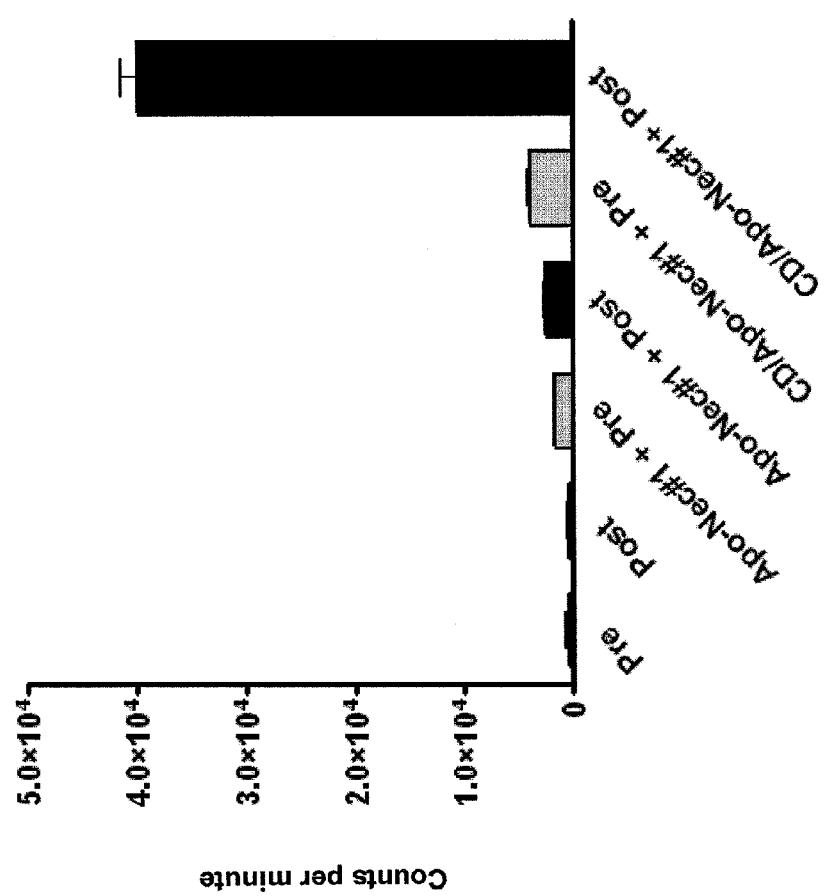
FIG. 3 shows in vitro e lymphocytes proliferation in response to autologous tumor cells presented by DC. Results are shown as mean±SD cpm (counts per minute) of triplicates. Lymphocytes with phytohemoaglutinin (PHA) incorporating more than $7 \times 10^4$ cpm were incubated as positive controls.

An autologous melanoma cell line was established for patient #1, and thus the likelihood of the application in such patient of the DC/Apo-Nec cells inducing an lymphocyte proliferation response against the own tumor cells could be assessed. Lymphocyte proliferation was assessed after 5 days lymphocyte incubation pre- and post-application with Apo-Nec#1 cells (irradiated tumor cells from patient #1 obtained as described in the examples). FIG. 3 shows that lymphocyte proliferation post-application as a response to DC/Apo-Nec#1 cells was higher compared to lymphocytes pre-application, which suggests that specific immunization to tumor antigens presented by Apo-Nec cells exists, which is also present in the patient #1 tumor after the application of DC/Apo-Nec cells.

Seven of the 15 patients enrolled in the study had haplotype HLA-A*0201 class I, and this allowed to study the restrictive HLA tumor-specific response in their own PBMC samples. Anti-gp100 response, and specific Melan A/MART-1 CD8+ T cells induced by the CD/Apo-Nec composition were assessed through the specific link of HLA tetramers/peptides, and the secretion de IFN-γ measured by ELISpot, directly in the peripheral blood samples.

Figure 4:
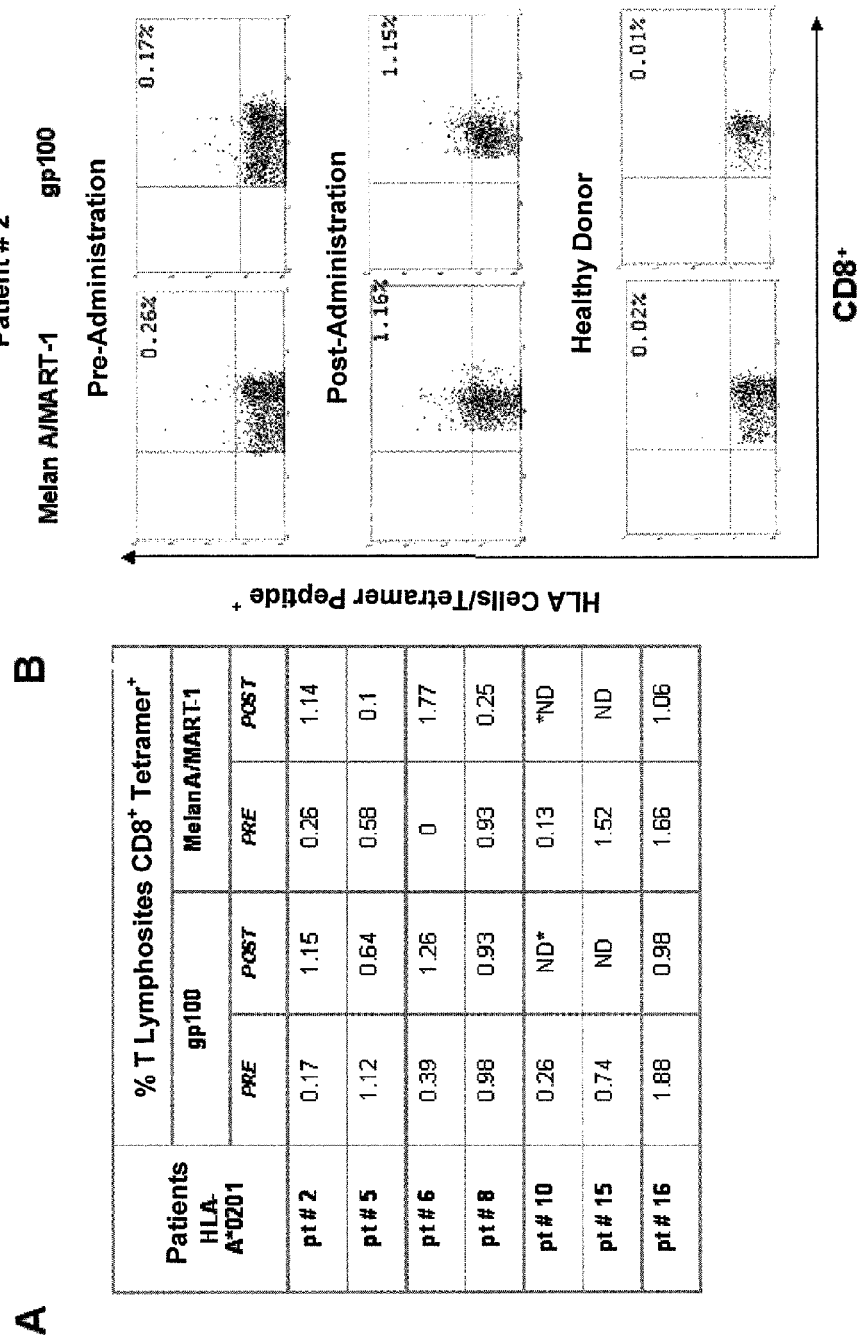
FIG. 4 shows tetramer staining for antigens Melan A/MART-1, and gp100. Panel A shows results obtained with PBMN samples from HLA-A*0201 patients participating in the test. *ND means: non-determined due to insufficient amount of CD8$^+$ T cells in the samples post-application. Panel B shows the increase of CD8+ HLA T lymphocytes/tetramer peptide+in PBMC from patient #2. Amounts represent percentage of CD8$^+$ HLA/tetramer peptide$^+$. HLA-A*0201 PBMC from healthy donors were stained as controls.

I 5/7 patients, sufficient PBMC were obtained pre (7 days before the first application) and post (15 days after the fourth application) in order to analyze presence of specific CD8+ T lymphocytes reactive to gp100, and Melan A/MART-1 by stain of tetramers. Results are shown in FIG. 4 A. Patients #2 and #6 increased significantly the frequency of gp100 and Melan A/MART-1 specific CD8+ T cells after application above 1%, and they were still NED (53, and 36 months, respectively, after the surgery), while patients #5, #8, and #16 reduced the pre-application tetramer coloration, and all of them progressed in the disease after the application (FIG. 3 A). An example is shown in FIG. 4 B, with the results of patient #2. The percentage of CD8+ T cells recognizing gp100, or Melan A/Mart-1 peptide increased after the application from 0.17 and 0.26 to 1.15, and 1.16, respectively. No reactivity was observed in an experiment performed in the same conditions with healthy positive HLA-A*0201 donors.

Release of IFN-γ was analyzed in an ELISpot of total PBMC pre and post-application after 24 hrs incubation with autologous DCs cells pulsed with gp100 or Melan A/MART-1, and using influenza peptides as control ($flu_{58-66}$). This assay was evaluated in 5/7 HLA-A*0201 patients. It was observed that two patients (#5 and #16) induced IFN-γ after the application of the DC/Apo-Nec composition of the invention, secreted by specific CD8+ T cells for gp100, and Melan a/MART-1. In patients #5, and #16, frequencies of 7-3.5× $10^{-4}$ CD8+ T cells secreting IFN-γ were induced. In patient #2, a great amount of specific CD8+ T cells for gp100, and Melan A/MART-1 were found before and after the application. This patient is still free from disease, 54 months after surgery. Patients #8, and #15 showed a low amount on base point (pre-application) and no changes were observed after four applications with the DC/Apo-Nec composition of the invention.

Figure 5:
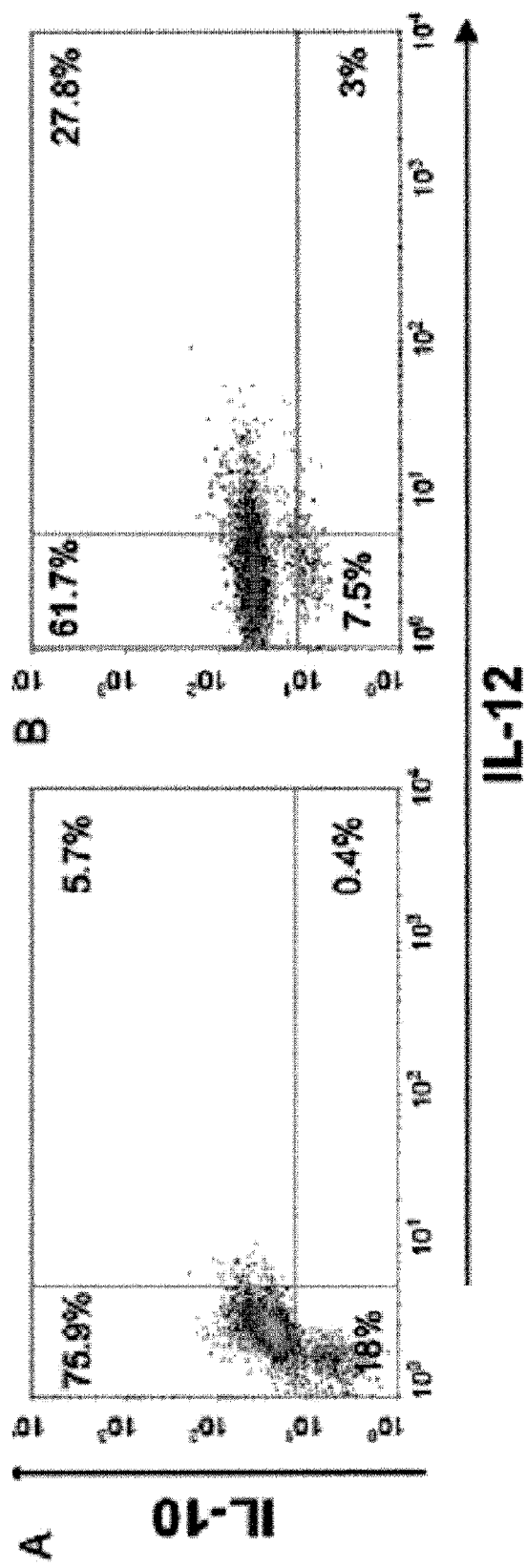
FIG. 5 shows intra-cytoplamic measurement of IL-10 and IL-12 in Apo-Nec cells of the invention. Panel A shows results of FACS from DCin, and panel B shows results of FACS from DC/Apo-Nec cells.

Balance between IL-12 e IL-10 in the DC/Apo-Nec cells of the invention was quantified by FACS in differentes times after phagocytosis, and followed by 8 hours treatment with Brefeldin A in order to accumulate cytokines intra-cytoplasmically. As shown in FIG. 5, only 6.1% of DCin produce IL-12, but after 32 hrs. From co-culture, 30.8% of DC/Apo-Nec cells was induced to produce IL-12. On the other hand, 81.6% of the DCin contained cytokines in the cytoplasm, and they were not modified after phagocytosis. Double positive cells producing IL-10 e IL-12 were 27.8% at 24 hours (see FIG. 5).

The DC/Apo-Nec composition of the invention was safe, and well tolerated by the patients.

The DC/Apo-Nec composition of the invention induced cell responses in patients, since the DTH reaction using Apo-Nec cells as immunogens increased in all patients after the second application, compared to base values.

85% of patients (stage IIc, and III) treated with the DC/Apo-Nec composition of the invention are free of disease after an average follow-up of 41.5 months, when treated after surgery (see FIG. 2). The DC/Apo-Nec composition of the invention is useful per se for the treatment of patients with melanoma, and is also useful as adjuvant after radical treatments, since it stimulates an immune response in the patient, where the immune system deletes all residual tumor cells, protecting the patient against possible recurrences. More specifically, the DC/Apo-Nec composition of the invention is useful for treating patients in stages IIB, IIC and III, who contain less tumor mass, and it is useful as adjuvant after radical therapies for stage IV patients.

It is evident for a skilled in the art that the DC/Apo-Nec composition of the invention may be used in treating human melanoma; it may also be used as adjuvant together with other treatments, and as immune system stimulant, for example depending on the stage of the patient and the stage of the treatment.

Importantly, it must be pointed out that the combination of Apo-Nec cells of the invention induces maturity of autologous DC cells. The mixture or combination of Apo-Nec cells of the invention is a good source of melanoma antigens to charge dendritic cells. Note that dendritic cells only mature by contacting, and phagocyting the combination of Apo-Nec cells of the invention, without adding an extra stimulus such as, for example Interleukine 1, Tumor Necrosis Factor α, CD40 ligand, or Prostaglandin E, which are commonly used as a maturation cocktail. DCs phagocyting the Apo-Nec cells of the invention increase migration in vitro in response to chemokine MIP-3β, and intracellular production of IL-12. The DC/Apo-Nec dells of the invention are capable of presenting crossed native tumor antigens to specific CTL antigens.

As mentioned above, phagocytosis of Apo-Nec cells by DCin of each patient induced maturity of such DC.

On the other hand, the cell lines of the invention were analyzed for their clonogenic ability. MEL-XY3 cell line colonies of the invention in soft agar present an heterogeneous morphology, with low adhesion between cells. A low proportion of melanotic colonies is observed. MEL-XY1 cell line colonies of the invention in soft agar present a compact morphology, with high adhesion between the comprised cells. Melanotic colonies are seldom observed.

Figure 6:
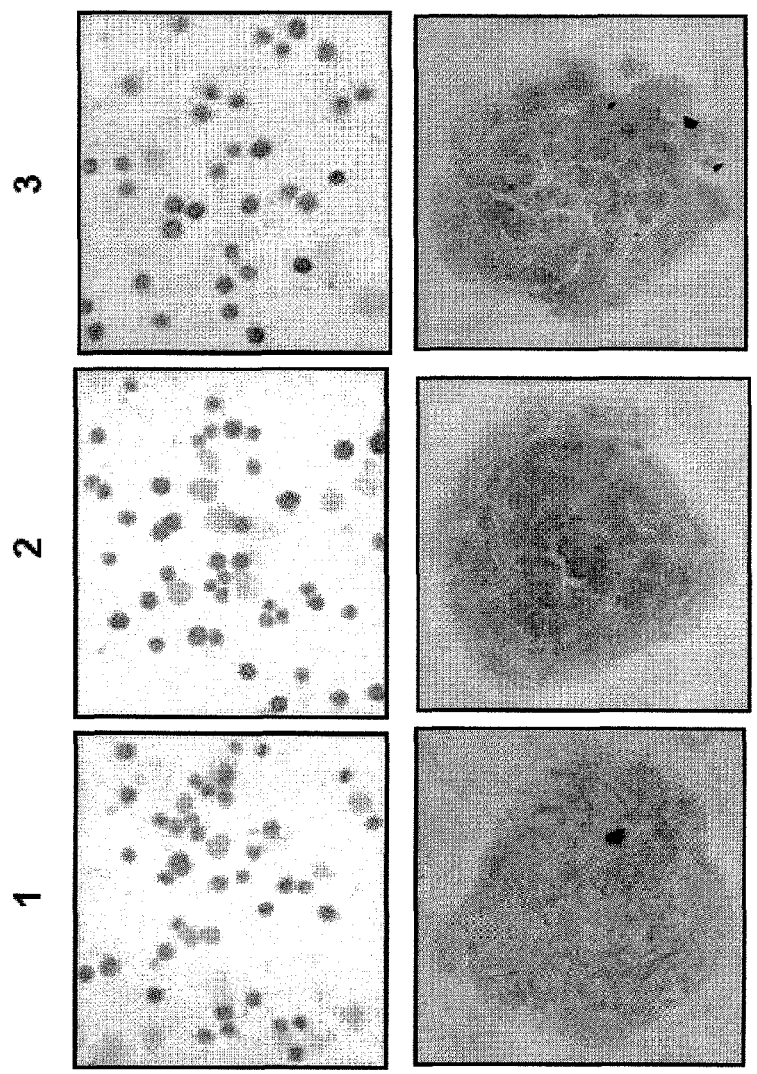
FIG. 6 shows antigen HMB45 and Mart-1 expression in line Mel-XY1 and in such cell line derivative clones. The three top panels correspond to the cell line, and the three lower panels correspond to the clones. Column 1 correspond to the cell line and control clones, column 2 correspond to the cell line HMB45 expression and the clones, respectively; and column 3 corresponds to the cell line Mart-1 expression and clones.

As a way of characterizing colonies, the melanoma antigen expression levels were compared, normalized to the expression of β-actin in the cell lines of the invention, and in such cell line colonies in soft agar. Clone characterization results are found in Table 4, and FIG. 6.

TABLE 4

Comparative study of antigen expression between cell lines of the invention, and clonogenic lines of the invention.

| Melanoma differentiation antigens | Cell lines | | | |
| --- | --- | --- | --- | --- |
| | MEL-XY3 line | MEL-XY3 colonies | MEL-XY1 line | MEL-XY1 colonies |
| MART1 | +++ | + | + | + |
| MAGE1 | + | ND | + | ND |
| NYESO-1 | ++++ | + | + | + |
| GP100 | + | ++ | + | + |
| TYR | + | ND | + | ND |
| TRP2 | +* | +* | +* | +* |
| B-ACTIN | + | + | + | + |

ND: non-determined
*Data not yet normalized

As may be observed, within the population, and each cell line of the invention a sub-population of de clonogenic cells exists, and these clonogenic cells are also included in the scope of the present invention. The presence of clonogenic cells may provide the patient with typical antigens of undifferentiated cells, also called stem cells.

Figure 7:
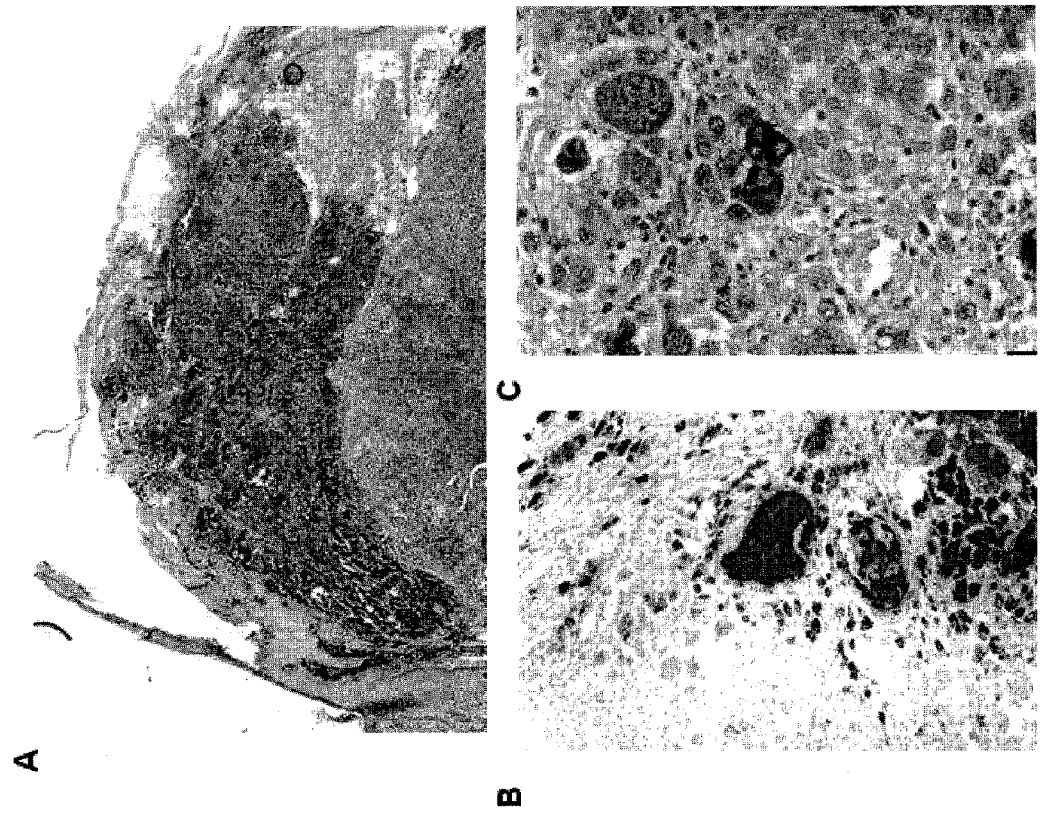
FIG. 7 shows a melanoma biopsy from patient #100. Panel A shows a low magnification image (25×), wherein Ag gp100 positive and negative tumor cells can be seen; panel B shows heterogeneous expression of gp100, wherein cells with high, moderate, and nil expression can be seen (400×); panel C shows heterogeneous Ag MART-1 expression, where a cell clone with high expression surrounded by negative cells can be seen (400×).

The heterogeneity of melanoma tumors is high, therefore for immuno-therapy it is fundamental to use complex antigen mixtures provided by the mixture, or combination of cell lines and their sub-populations. As an example, FIG. 7 shows a primary melanoma biopsy evidencing the heterogeneity of such tumors compared to the expression of melanocytic differentiation antigens.

When patients were treated with the Apo-Nec composition of the invention together with BCG as adjuvant, and GM-CSF as immuno-modulator according to the scheme disclosed below in the examples, it was observed that 75% of patients (stages IIC and III) were free of disease with a maximum follow-up of 51 months (see FIG. 8), and toxicity was low, and only of degree 1.

Figure 9:
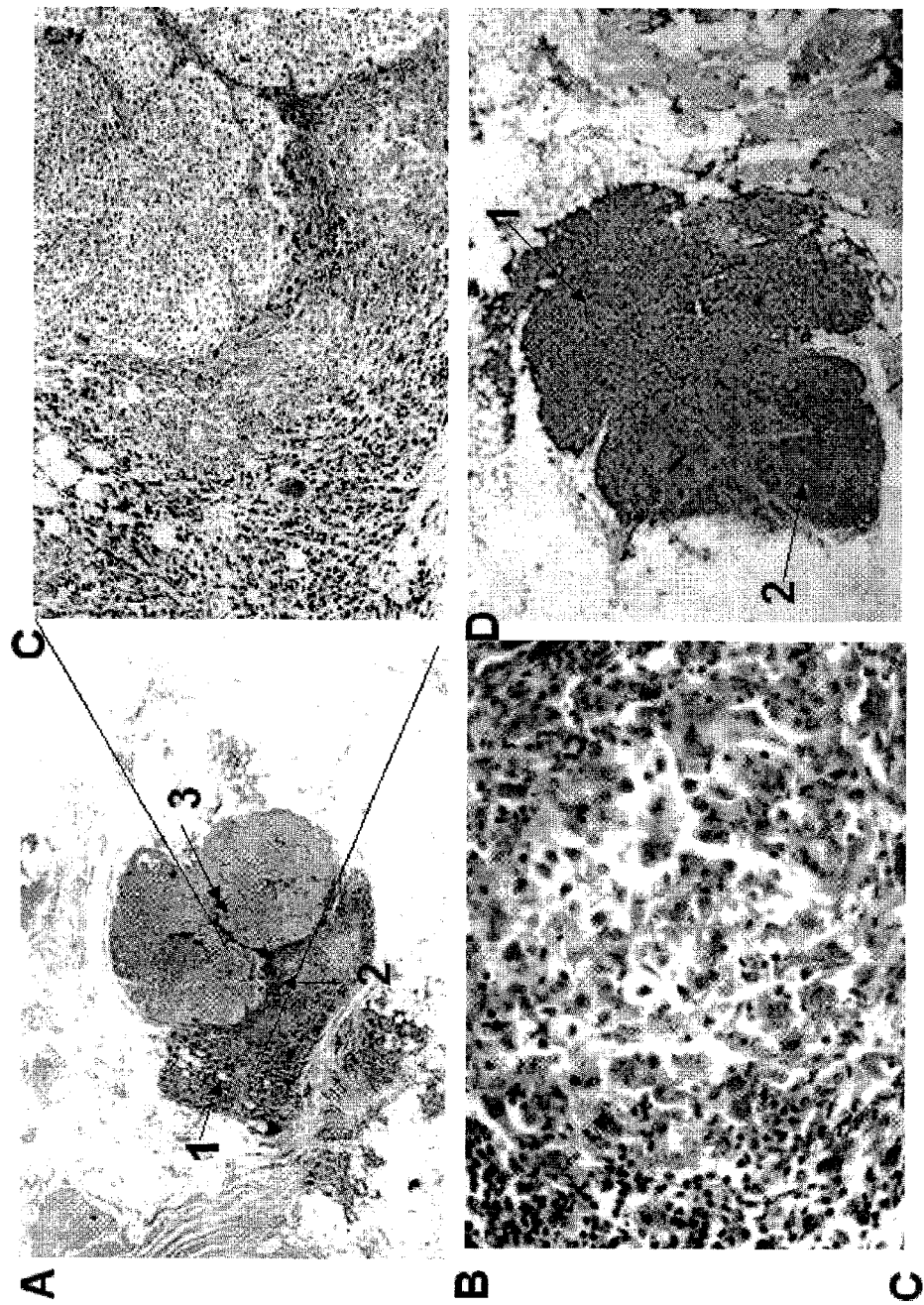
FIG. 9 shows dermal metastases excised from patient #200, treated with the Apo/Nec composition of the invention, in addition to GM-CSF and BCG. Panel A shows macrophages in the necrotic area of the tumor (1), infiltrated with de lymphocytes in contact with tumor cells (2), and a viable tumor area (3). Panel B is a 100× detail of the area of strong tumor infiltration, panel C is a 400× detail of the same area, wherein infiltrating lymphocytes are observed, panel D shows a detail of the same metastasis wherein most of it is necrotized with macrophages charged with melanin (1), and a viable area (2) (25×).

Exemplary results from one selected protocol patient are shown. Patient #200 is female, Caucasian, 67 years old, appeared in November 2003. In June 2002, she was subjected to surgery on an increased dorsal nevum. Histology disclosed a cutaneous melanoma, Clark's level IV, Breslow's level 5.7 mm. In August 2002, some satellitoses were detected, which were excised. Patient was administrated Apo-Nec+BCG+ GM-CSF, receiving 600 µg GM-CSF (per composition) and finished treatment with little toxicity. At the last clinical examination, a suspected node was detected on the back, which was excised, and the microscopic image is shown in FIG. 9. Intensive lymphoid infiltration is observed, with viable tumor areas remaining, but also intensive tumor tissue necroses, and the presence of macrophages charged with melanin.

As an example, the results in a patient treated with the Apo-Nec composition of the invention+BCG+IFN-α are also shown. Patient #300 is male, 17 years old, who appeared with left inguinal adenopathy. Two months later, another left inguinal excision was performed, where 4/11 nodes with melanoma metastases were obtained. He received treatment with interleukin-2 in low doses.

Figure 10:
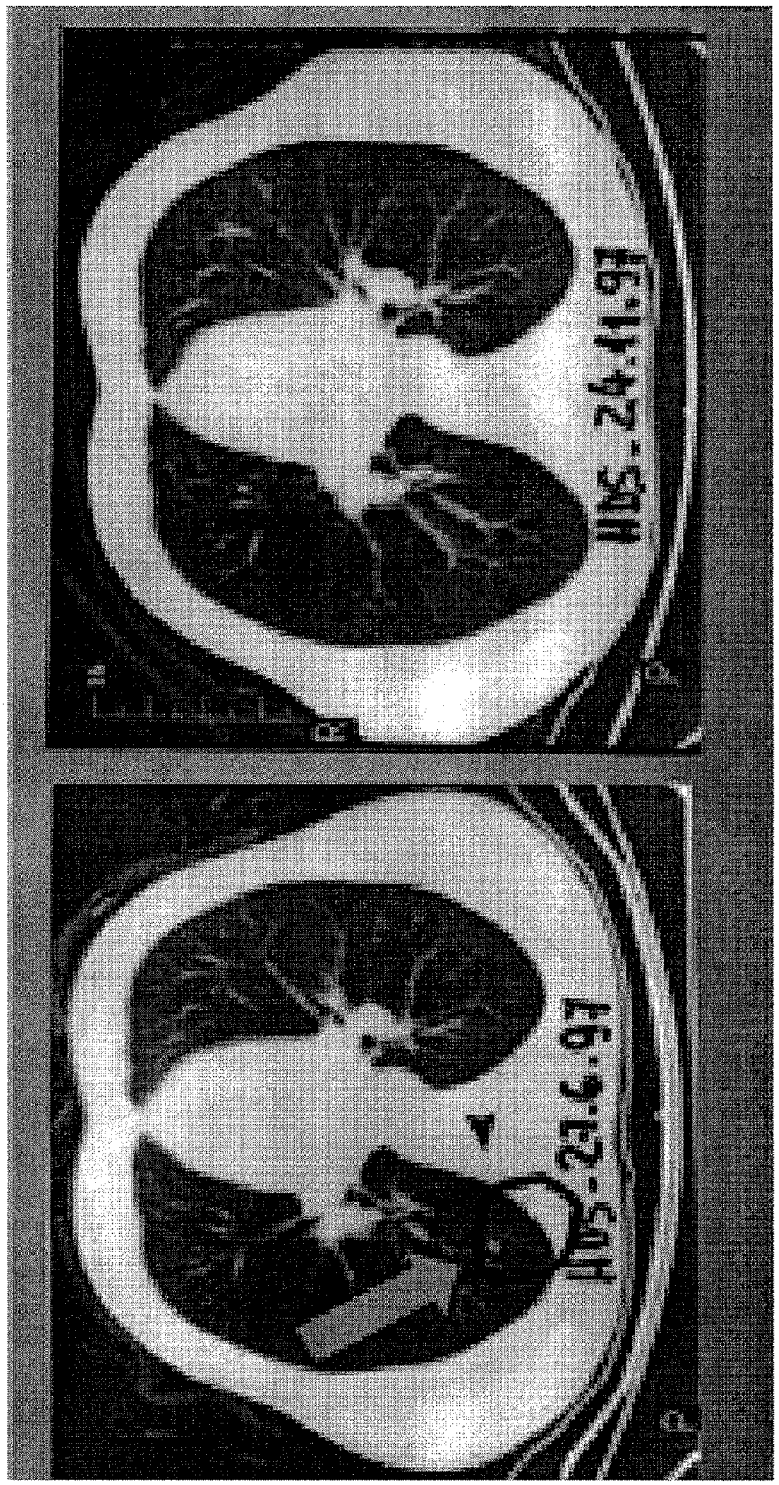
FIG. 10 show computerized axial tomography images from patient #300, treated with Apo-Nec composition of the invention in addition to BCG. Panel A shows with an arrow the location of lung metastasis, and panel B shows an axial tomography image taken 5 months later.

14 months after the second excision, recurrence was detected in left inguinal arch, and again a surgery was performed, where 5/7 nodes with melanoma metastases where isolated. The patient presented back pain. Computed axial tomography disclosed retroperitoneal adenopathies, and chemotherapy with Dartmouth scheme was performed. After finishing chemotherapy, he began treatment with Apo-Nec composition of the invention+BCG. 14 months after beginning treatment with the composition of the invention, a node was detected in the left inguinal area. He was subjected to surgery, and melanoma metastases were detected with large lymphoplasmocyte infiltration. The patient continued treatment with Apo-Nec composition+IFN-α. FIG. 10 shows the remission of a left lung node. Currently, the patient is disease-free.

The present invention discloses melanoma cell lines, which in combination express most melanoma-associated antigens, compositions comprising such irradiated lines, and compositions comprising autologous DC generated ex vivo, which have phagocyted a mixture of apoptotic/necrotic cells of the melanoma cell lines.

This invention is better illustrated according to the following examples, which must not be understood as a limitation imposed to its scope. On the contrary, it must be clearly understood that other embodiments, modifications, and equivalents may be referred, which after reading the present description, may be suggested to skilled in the art without leaving the spirit of the present invention and/or the scope of the attached claims.

Example 1

Obtaining, Establishment, and Maintenance of Cell Lines of the Invention

Mel-XY1: Line Mel-XY1 was obtained from a male Caucasian patient, from a lung metastasis secondary to a primary melanoma on the back. The patient died two years later due to brain metastases.

Mel-XY2: The patient from whom the line originated was 44 years old, and was a Caucasian male who presented ulcerated melanoma on the back (Clark's level III). Two years later, he developed simultaneous axillary adenopathies, and lung metastases. The axillary adenonopathies were excised, dissociated, and such cells gave rise to the cell line.

Mel-XY3: The patient was a Caucasian 43-year-old male, who had developed a primary arm melanoma. Two years later, axillary lymphatic node metastasis appeared. The patient received chemotherapy with DTIC, without apparent clinical response. The axillary metastases were excised, and the cells gave rise to cell line Mel-XY3.

Mel-XX4: It was obtained by surgery of an inguinal adenopathy in a white 33-year-old woman, where such adenopathy was diagnosed as melanoma metastasis. The primary tumor was unknown. Fifteen months later, the patient had a recurrence in the inguinal lymphatic node. The gross melanotic node was excised, cut into small pieces, the fat and connective tissue were removed, and was suspended in Dulbecco modified by Eagle's Medium (DMEM), mechanically separated by pressure on a nylon mesh, and the cell aggregates were treated enzimatically overnight at 37° C.

The cells were re-suspended in melanoma culture medium supplemented with 10% fetal bovine serum (FBS) (Natocor, Cordoba, Argentina), sown in 25 cm² culture flasks, and incubated at 37° C. with humidity, and a 5% $CO_2$-95% atmosphere in air. After 24 hrs, the culture medium was removed in order to eliminate non-adhered cells.

The cell suspension was passed four times through anti-fibroblast micro-sphere columns (Miltenyi Biotec, Germany). The cells obtained were named Mel-XX4

Maintenance of the four cell lines of the invention (Mel-XY1, Mel-XY2, Mel-XY3, and Mel-XX4) was done through culture in melanoma medium DMEM: F12 nutritive mixture (1:1) supplemented with 2 mM glutamine, 20 nM sodium selenite, 100 μM ascorbic acid, 0.3 mg/ml galactose, 0.15 mg/ml sodium piruvate, and 5 μg/ml insulin), 100 IU/ml penicillin, 10 μg/ml streptomycin, in addition to 10% fetal bovine serum (FBS) (Natocor, Cordoba, Argentina) at a GMP laboratory of Centro de Investigaciones Oncológicas-FUCA.

Clones CTL (restricted HLA A*0201) specific for Melan A/MART-1 (M27: AAGIGILTV), and gp100 (G154: KTWGQYWQV) antigens were expanded in RPMI medium with 10% inactivated AB human serum, and antibiotics, in 14-days-cycles using 30 ng/ml antibody anti-CD3 (OKT-3, BD Biosciences), and series of 300 UI/ml IL-2 (Chiron BV, Amsterdam, Netherlands) every 3 days.

Example 2

Cell Line Characterization

Growth Kinetics In Vitro:

$10^4$ cells were cultured by well in 24-well plates (Corning). Every 2-3 days, the cells were treated with EDTA (0.02%), harvested, and counted. The population duplication time was esteemed from the growth curve slope during the exponential phase.

Clonogenicity

Anchoring-independent cell growth was determined by the soft agar method (Hamburger, and Slamon, Science 197: 461, 1977). $3-10 \times 10^3$ cells were cultured in the upper layer. The plates were incubated for 21 days, and then fed each day with 50 μl culture medium. Colonies with over 36 cells were counted under the microscope.

Characterization of Melanoma Antigens by Immuno-Citochemistry (ICC) and FACS

For the ICC evaluation, the exponentially growing cells were treated with EDTA, centrifuged, fixed with formaldehyde, embedded in paraffin, and cut into fine sections. Normal tissue samples from the patient were used as control.

Tissues and cells were assayed with monoclonal antibodies (Mabs) against keratins, vimentin, and gp100/HMB 45 (Biogenex), MART1/Melan-A (Dako), and with polyclonal antibodies anti-S100 (Biogenex).

Reactions were visualized with avidin-biotin complexes (Vectastain ABC). Endogenous peroxides were blocked with 0.6% $H_2O_2$.

Indirect immunofluorescence reactions were carried out by re-suspending EDTA-treated cells. After blocking with normal goat serum diluted 10%, the cells were incubated with primary antibodies, washed, incubated with secondary antibodies (FITC anti-mouse goat immunoglobulin (Dako), washed, fixed in 1% para-formaldehyde, and analyzed by FACS (FACS Vantage SE, Becton-Dickinson, USA). Primary antibodies were murine anti-p53 Mabs (DO-7, BD Pharmingen), 3F8 anti-GD2, R24 anti-GD3. In the case of p53, the cells were permeatized. Human leukocyte antigens (HLA) Class I, and Class II were typified by PCR-SSP.

Melanoma Associated Antigen Determination by RT-PCR:

Total RNAS was extracted with Trizol (Invitrogen). In order to initiate cADN synthesis, the appropriate primers were added to 1-3 μg RNA, and incubated with 200 U MMLV-RT enzyme (Promega), 25-40 U RNAsin (Promega), and 250-500 μM dNTPs (Invitrogen) for 5 min at 70° C., and then for 60 min at 42° C. cDNA aliquots (2-10 μl) were amplified with Taq DNA polymerase (Invitrogen), using specific pairs or primers.

Specific primers are shown below:

```
Gp100
5'-GCTTGGTGTCTCAAGGCAACT-3'        (SEQ ID N° 1)

5'-CTCCAGGTAAGTATGAGTGAC-3'        (SEQ ID N° 2)

MART-1
5'-CAAGATGCCAAGAGAAGATGCTCACT-3'   (SEQ ID N° 3)

5'-GCTTGCATTTTTCCTACACCATTCCA-3'   (SEQ ID N° 4)

Tyrosinase
5'-TTGGCAGATTGTCTGTAGCC-3'         (SEQ ID N° 5)

5'-AGGCATTGTGCATGCTGCTT-3'         (SEQ ID N° 6)

5'-GTCTTTATGCAATGGAACGC-3'         (SEQ ID N° 7)

5'-GCTATCCCAGTAAGTGGACT-3'         (SEQ ID N° 8)

TRP-2
5'-GAGTGGTCCCTACATCCTACG-3'        (SEQ ID N° 9)

5'-GCGTCCTGGTCCTAATAATGT-3'        (SEQ ID N° 10)

MAGE-1
5'-GAGTCCTCAGGGAGCCTCC-3'          (SEQ ID N° 11)

5'-TTGCCGAAGATCTCAGGAAA-3'         (SEQ ID N° 12)

NY-ESO-1
5'-AGCCGCCTGCTTGAGTTCTACCTC-3"     (SEQ ID N° 13)

5'-AGGGAAAGCTGCTGGAGACAG-3'        (SEQ ID N° 14)

MDR-1
5'-TCCAAGAAGCCCTGGACAAAG-3'        (SEQ ID N° 15)

5'-TTGATGATGTCTCTCACTCTGTTCC-3'    (SEQ ID N° 16)

MIA
5'-CATGCATGCGGTCCTATGCCCAAGCTG-3'  (SEQ ID N° 17)

5'-GATAAGCTTTCACTGGCAGTAGAAATC-3'  (SEQ ID N° 18)

β-actin
5'-ATGTTTGAGACCTTCAACACCCC-3'      (SEQ ID N° 19)

5'-GCCATCTCTTGCTCGAAGTCCAG-3'      (SEQ ID N° 20)
```

Anti-sense primers are shown in the lower line.

For tyrosine detection, a 1/100 aliquot from the first PCR reaction with internal primers (nested PCR) was also amplified.

PCR products were analyzed in agarose gels, and stained with ethidium bromide; the size of the fragments was calculated by comparison with the rum sown with 100 bp DNA PM markers (Promega).

Cytogenetic, and Cytomolecular Analysis:

Cells corresponding to the four lines of the invention were incubated for cytogenetic analysis in exponential growth colchicine (0.1 µg/ml) at 37° C. for 8-16 hrs, collected with a Trypsine-EDTA solution, and processed according to standard protocols. The G-band technique was used. Chromosome identification was done according to International System for Human Cytogenic Nomenclature (Mitelman, 1995 ISCN.: An International System for Human Cytogenetic Nomenclature, (ed. S Karger, Basel).

Example 3

Generation of Dendritic Cells (DC) from Monocytes, Characterization Thereof, and Charge with Apo-Nec Cells The dendritic cells were obtained form buffy-coats or leukopheresis products from healthy donors. Peripheral mononuclear cells (PBMCs) were purified with a Fycoll-Hypaque density gradient. PBMCs were suspended in fresh AIM-V™ serum-free medium (Invitrogen), and were left adhering in culture flasks (TPP, Germany). After 2 hrs at 37° C., non-adherent cells were removed, and adhered monocytes were cultured for 5 days in AIM-V supplemented with 800 U/ml rhuGM-CSF and 50 ng/ml IL-4 (Peprotech, Mexico), thus obtaining CDin. Phenotype changes were analyzed by light microscope and FACS. To induce DCin controlled maturation 2 µg/ml LPS (E. coli J5 lipopolysaccharides, Sigma, St. Louis, Calif.), and finally cells were cultured for 48 hrs.

DC cell phenotype characterization was performed when cells were in immature state (DCin), and after apoptotic/ necrotic cell (Apo-Nec cells) phagocytosis assays through staining of $5 \times 10^5$ cells with antibodies marked with fluorochromes against CD14, CD11c, CD1a, HLA class II, CD80, CD86, CD83, CD40, HLA class I, and CCR7 antigens (BD Biosciences, San Jose, Calif.), through FACS analysis (Becton Dickinson, San Jose, Calif.). Appropriate iso-type controls were rat IgG2a PE, and mouse IgG1 and IgG2a (BD Biosciences, San Jose, Calif.). The expression of CD83 in DCs phagocyting Apo/Nec cells was also analyzed, employing non-marked monoclonal antibody anti-CD83 (IgG1), and the appropriate iso-type as control; for developing, an anti-mouse IgG1-PerCP (BD Biosciences, San José, Calif.) was used.

DC endocytosis capacity was assessed by incubating $1 \times 10^6$ DCs with 1 mg/ml conjugated Dextran with FITC (Dx-FITC) (Sigma, St Louis, Calif.) for 30 min at 37° C. After incubation, the cells were washed with PBS, and analyzed by FACS. Controls included DCs incubated with Dx-FITC for 30 min at 4° C. in order to inhibit the endocytosis process; on the other hand, basal incorporation basal was considered at time 0 of the assay. DX-FITC incorporation (endocytosis) was quantified by FACS.

Assessment of DC Cell Phagocytosis:

DCin cells were co-cultivated with Apo-Nec cells (prepared as shown above) in fresh AIM-V medium on different times. In some assays, DCs were stained red with PKH26, and the Apo-Nec cells were stained green with PKH67 (Sigma, St. Louis, Calif.). Analysis by FACS was performed after co-culture, and the percentage of DCs phagocyting Apo-Nec cells was defined as the percentage of double positive cells. Appropriate controls were performed for each color. The control of non-specific bond of Apo-Nec cells with DCs was performed by incubating cells at 4° C. for the same periods of time.

DCs In Vitro Migration:

DCs in vitro migration was assayed before and after co-culture with Apo-Nec cells, using 48-well chemotaxis chamber (AP 48 Neuroprobe Inc., Gaithersburg, Md.). 10 ng/ml de MIP-1α, or MIP-3β (Peprotech, Rocky Hill, N.J., USA) diluted in RPMI were placed in the bottom compartment. Basal migration was assayed by placing RPMI in the lower chamber. DCs were sown in the upper chamber ($3 \times 10^4$ CDs/ well) in RPMI. A 5 µm-pore poly-carbonate membrane was placed between the upper and the lower chamber (Neuroprobe, Inc., Bethesda, Md.). After 90 min at 37° C., cells of the upper side of the membrane were removed, and cells migrating adhered to the lower side of the membrane were stained with Giemsa 10% diluted in neutral water. Membranes were air-dried, mounted on a slide with Canada balsam, and the migrating runs were counted using a microscope. Five fields per well were analyzed with 40× magnification, and 3 wells/condition were analyzed. Statistical analysis was performed by Student's Test.

Electronic Microscopy:

The phagocytosis process was also studied by electronic microscopy. Co-culture samples were fixed with 2.5% glutaraldehyde in 0.1 M phosphate buffer, and the post-fixation staining with 1% osmium tetroxide was carried out, they were washed twice with distilled water, and counter-stained with 5% uranil acetate for 2 hr. After washing, and dehydration, the samples were embedded in resin (Durkupan). Ultra-thin sections were obtained (70-90 nm), mounted on copper meshes, and counter-stained with Reynold's lead citrate. Meshes were analyzed in a Zeiss 109 transmission electronic microscope. Alternatively, in order to obtain figures of the complete cells, thin sections (0.5 µm) were obtained in a ultra-microtome (Reichert-Jung), stained with 0.4% toluidine blue, 0.1 M carbonate buffer, mounted on Durkupan, and analyzed with light microscope (1000×). Images were obtained with a Sony Cybershot Digital camera (5 megapixels), and processed with Adobe photoshop 6.0 program.

In Vitro Cross Presentation Assay, IFN-γ Secretion:

98% CD14+ monocytes were purified from HLA A*0201 donors using anti-CD14 micro-spheres (Miltenyi Biotec, Germany), and differenciated to DCin cells by 5 days culture as described above. DCin cells were incubated with Apo-Nec cells for 6, 12, 24, and 48 hrs, and exposed overnight to specific CTL MelanA/MART-1, or gp100 clones in 1 ml AIMV medium. IFN-γ secretion to supernatant was determined in triplicate by the ELISA technique (OptEIA IFN-γ, Pharmingen BD Biosciences, San Diego, Calif.) according to the supplier's suggestions. A calibration curve was drawn for each experiment, and sample concentration was calculated using a log-log regression analysis, and using Cembal 2.2 software. Controls included: DCs plus 20 µg/ml MART-1 or gp100 peptides, HLA A*0201+ viable melanoma cell lines expressing MART-1, and gp100 antigens (positive controls) or DCs cells cultivated with non-specific peptides, and HLA A*0201+ viable melanoma cell lines not expressing the appropriate antigens (negative controls).

Measurement of Introcytoplasmic Cytokines IL-10 e IL-12:

DCs marked with PKH26 (red) were co-cultured with Apo-Nec cells marked with PKH67 on different times (6, 12, 24, and 48 hrs). Accumulated cytokine measurement was done by the intracellular immunofluorescence technique, after blocking the output thereof with Brefeldin A (8 hrs) post-culture (Golgi Plug, BD Biosciences, San Jose Calif.). The cells were permeatized with 0.05% saponin, and stained with anti-IL10 (rat isotype IgG2a)-APC, and anti-IL12 sub-unit p40-p70 (mouse isotype IgG1)-PerCp (BD Biosciences, San Jose, Calif.). Double stained PKH26/PKH67 population was selected for studies by FACS, and cytokines were assessed for such population in a four color experiment. Co-culture at 4° C. was used as control.

Example 4

Preparation of Compositions of the Invention, and Application Schemes

Apo-Nec Composition:

Irradiation of Cell Lines:

The four cell lines of the invention (Mel-XY1, Mel-XY2, Mel-XY3, and Mel-XX4) were irradiated with gamma radiation at 70Gy (Siemens, Instituto Alexander Fleming, Buenos Aires, Argentina), subsequently the cells were frozen (50% DMEM, 40% human albumin, and 10% DMSO) in liquid nitrogen until use.

The day of cell application, they were thawed, washed, and prepared in composition doses containing between $5-10 \times 10^6$ cells of each of the isolated cell lines of the invention, or combinations thereof, re-suspending them in DMEM medium.

300 ul were injected intradermally.

DC/Apo-Nec Composition:

Preparation of Apoptotic/Necrotic Tumor Cells:

Irradiated and frozen cells (Mel-XY1, Mel-XY2, Mel-XY3 and Mel-XX4) as described above were thawed and sown in melanoma medium plus 10% fetal bovine serum until complete apoptotic process. After 72 hrs culture, the cells were detached from the bottom of the flasks, washed, counted, and re-suspended in fresh AIMV™ medium free of serum (therapeutic grade, GIBCO, Invitrogen Corporation, Grand Island, N.Y.). Apoptosis and necrosis was assayed by the Anexin-V FITC link technique, and incorporation of propidium iodide (IP) (Anexin-V apoptosis detection kit, BD Biosciences, San Jose, Calif.), and analyzed by FACS. Clonogenig assays in soft agar were performed in sextuplicate ($1.5 \times 10^4$ cells/well) in order to analyze proliferation capability in irradiated cells, compared to non-irradiated control cells.

5, 10, 15, o $20 \times 10^6$ DCs, according to each patient's dose, were co-cultured with Apo-Nec cells in AIMV medium for 48 hrs at 37° C. On application day, co-cultivated cells were centrifuged at 1200 rpm for 5 min, re-suspended in DMEM medium (300 µl), and injected intra-dermally in one of the four extremities with intact drainage of lymphatic nodes.

Quality controls, and sterility assays were done for all composition preparations.

Example 5

Patient Study Design, and Selection Criteria

Studies in patients were carried out to assess toxicity, viability, and immune response to treatment. The studies were approved by the Institutional Revision Council of Instituto Alexander Fleming, and by an ethics commission. Viability criteria were (a) cutaneous melanoma, confirmed by histology in stages IIB, IIC, III, or IV (AJCC); (b) patients with minimal or non-detectable disease (ND) after surgery, assessed Computed Axial Tomography, and lactate dehydrogenase (LDH) enzyme values. Patients with unknown primary melanoma could be included in the study; (c) age between 15, and 60 years; (d) life expectation >6 months; (e) yield (ECOG) 0, o 1; (f) patients of stage III preciously treated with IFN-α who had finished or interrupted treatment due to disease progression, toxicity, or any other clinical cause, or patients who had not initiated treatment with IFN-α six months prior to the surgery; (g) adequate venous access for the leukopheresis procedure, (h) laboratory election criteria were: hemoglobin >10 gr %; white blood cell count >4800/mm$^3$, platelets >150,000/mm$^3$; total and direct bilirrubin, oxalacetic transaminases, glutamic-piruvic transaminase <1.5 times normal highest value; LDH ≦450 mU/ml; i) non-pregnancy, with serum β-HCG determined one week before each application in pre-menopausal women; (i) creatinine <1.4 mg %; (k) no chemotherapeutic, radiotherapy treatment, or biological treatment for the previous month; (k) no medication with corticosteroids, or non-steroid anti-inflammatory medication (AINEs); (1) no active brain metastasis; (m) normal ECG; (n) all patients had to sign informed consent.

Patient Assessment and Treatment Scheme:

Patient basic assessment was done within 35 days before the first application. Clinical evaluation included complete clinical history, physical exam, electrocardiogram (ECG), Computed Axial Tomography (thorax, abdomen, pelvis, and brain), determination of tumor stage, tumor size, and documentation of sites of disease, chemical blood test, and hematology. The selected patients were subjected to leukopheresis in order to obtain PBMC, to generate DCs.

Patients received 4 applications of DC/Apo-Nec with 2 weeks intervals. Inoculation was done intradermally (300 μl), and with each dose DTH test were assayed consisting in inoculation in the forearm of between 5, and $20 \times 10^6$ DC/Apo-Nec cells without adjuvant. Vital signs and DTH skin reactions were analyzed at 2, 24, and 48 hrs post-application. Patient status was investigated on day 70 by abdominal ultrasonography, and thorax X-rays, and the protocol was ended on day 75 with a clinical exam.

For the application of Apo/Nec cells of the invention, patients were injected intradermally (id) in one extremity with intact lymphatic nodes. Twenty (20) patients received a 400 μg rhGM-CSF dose (100 μg per day, four days). On the day of application, 0.1 ml hGM-CSF were mixed with Apo-Nec ($16 \times 10^6$ irradiated cells in 0.3 ml), and BCG ($1 \times 10^6$ colony forming units) in 0.05 ml. During the following 3 days, 0.1 ml rhGM-CSF were injected i.d. on the application site. Each patient received 4 applications separated by 3 weeks, then 1 composition every two months for a year, 1 composition every three months the second year, and continued afterwards with 1 composition every 6 months.

Statistical Analysis:

All adverse results were classified according to Common Toxicity Criteria for National Cancer Institute (NCI).

The assessable population was defined as all patients receiving the four applications. Since most patient data were not normally distributed, the total data were analyzed using the Wilcoxon's Rank Sum test. DTH values of the different groups receiving different amount of DCs/Apo-Nec were compared between each group with one variable ANOVA, and the Dunnett multiple comparison test. A $P<0.05$ value was considered significant.

Methods to Evaluate Immune Response of Treated Patients:

To evaluate patient immune response, serum was obtained on day 7 before application (pre-serum), and day 15 after finishing treatment (post-serum), and the samples were stored at −80° C. PBMC cells were purified by a Ficoll-Hypaque gradient, and subsequent centrifugation form leukopheresis (pre-application), or from 100 ml blood obtained 15 days after the last dose (post-application), PBMC were frozen in 50% DMEM, 40% human albumin, and 10% DMSO until use in immunologic assays. HLA-A*0201 HLA typification was determined after incubating patient samples with mouse anti-HLA*A0201 monoclonal antibodies conjugated with FITC (BD-Pharmingen, San Jose, Calif.).

DTH Reaction:

On each application day, a DTH test was done in the forearm with $2 \times 10^5$ Apo-Nec cells, and the reaction was evaluated at 2, 24, and 48 hrs post-application. DTH intensity value was established as follows: 0: erythema <0.5 cm; 1: macular erythema 0.5-1.0 cm; (2) macular erythema 1.0-2.0 cm; 3: macular erythema >2.0 cm, or papular erythema <1.5 cm; 4: papular erythema >1.5 cm. Store DTH corresponds to the sum of all individual DTH intensities/4.

Proliferation Assay:

Pre- and post-composition PBMC were obtained by a Ficoll-Hypaque density gradient, and stored frozen in liquid nitrogen until use. The cells were thawed for the assay, and incubated in AIM-V medium (Gibco, Grand Island, N.Y.) for 1 hr at 37° C. $5 \times 10^5$ cells were sown in 96-well plates in the presence or in absence of phyto-hemoaglutinin (PHA) (5 μg/ml) (Gibco, Grand Island, N.Y.), and incubated at ° C. for 72 hrs. During the last 16 hrs, the cells were pulsed with (3H)dThd (Amersham, 1 μCi/well), and after cell lysis, the DNA incorporated radioactivity was measured (Cell Harvester, Nunc, Rochester, N.Y.), with a liquid scintillation counter.

Determination of Cytokines:

Patient serum IL-10 and IL-12 concentrations were determined before the application (pre-application serum), and two weeks after the fourth application (post-application serum). Sera were frozen at −80° C. until ELISA assay (OptEIA IL-10 and IL-12, BD Biosciences, San Diego, Calif.) was performed. A calibration curve was drawn for each assay, and the sample concentration was calculated by log-log linear regression analysis using Cembal 2.2 software.

Measurement of IFN-γ by ELISpot Technique:

CD14$^+$ cells were purified as stimulators from PBMC from HLA-A2 positive patients using micro-spheres covered by anti-CD14 (Miltenyi Biotec, Paris, France), cultivated 5 days in synthetic SYN-H medium (AbCys, Paris, France) with 100 ng/ml GM-CSF, and 20 ng/ml IL-4, and matured with 10 μg/ml LPS for additional 48 hrs. Mature DCs were pulsed for hr at 37° C. with 10 μg/ml of the appropriate peptide diluted in SYH-H medium, washed, and mixed with PBMC until reaching an relation E/T patients of 10:1, using a total of $10^5$ CD8+ lymphocyte cells/well.

96-well plates were covered with nitrocellulose (MAIPS 450; Millipore, Bedford, Mass.) overnight at 4° C. with 10 μg/ml human anti-IFN-γ mAb (Mabtech, Nacka, Sweden) in carbonate-bicarbonate buffer, pH 9.6, washed, and blocked with IMDM medium+10% AB human serum (Biowest, Nuaille, France) for 1 hr at 37° C. Effector cells were sown in 100 μL medium, and target cells were added until reaching an E/T relation of 10:1, at a total of 200 μL/well. After 24 hrs incubation, the wells were washed 5 times with 0.1% Tween-20 in PBS. Plates were incubated 2 hrs at room temperature with 1 μg/ml human biotinilated anti-IFN-γ mouse mAb (Mabtech) in PBS/HSA (0.4 g/L). After several washings with 0.1% Tween-20 in PBS, 1:1000 alkaline phosphatase-streptavidine (Mabtech) in PBS/HSA was added, and incubated for 1 hr at room temperature. Then the plates were washed, and the 5-bromine-4-chlorine-3-indol phosphate/nitro-tetrazolium blue substrate was added for 30 minutes at room temperature (Mabtech). Development of color was quenched by washing the plates with water. After drying, the CD8+ T cells secreting IFN-γ were counted, visualized by a color spot on the nitro-cellulose membrane, using the ELISpot automatic image system reader (AID, Strassberg, Germany).

Staining with HLA Tetramers/Peptides:

HLA-A0201 tetramers were used to identify clones of specific CD8+ T lymphocytes for MART-1 (AAGIGILTV), or gp-100 (KTWGQYWQV) conjugated to PE (phycoerithrine), or APC (allo-phycocyanine) respectively. The staining procedure was done at 37° C. for 15 minutes, and immediately placed on ice. Then, the samples were incubated with anti-CD8 FITC (BD Biosciences, San Jose Calif.) at 4° C. for additional 40 minutes, and analyzed by FACS. Positive controls were done with specific CTL clones (restricted HLA A*0201) for MART-1 (M27: AAGIGILTV), and gp100

(G154: KTWGQYWQV) antigens expanded un 14 day-cycles in RPMI medium in the presence of anti-CD3 antibodies (OKT-3, BD Biosciences) at 30 ng/ml, and series of IL-2 (Chiron By) a 300 UI/ml each 3 days, plus 10% inactivated human AB serum, and antibiotics. Negative controls were performed PBMC samples from healthy HLA-A0201 donors.

Determination of Humoral Response:

Viable cells comprising Apo-Nec cells were mixed in equal en proportions, blocked with 10% rabbit serum for 30 min, and incubated with pre- and post-application serum, diluted 1/10 per 1 hr at 4° C. Then they were washed, and the cells were incubated with a human anti-immunoglobulin antibody (IgG+A+M) obtained in rabbits (DakoCytomation, Glostrup, DK) for 1 hr at 4° C. The cells were washed, fixed in para-formaldehyde at 1%, and were analyzed by FACS. Alternatively, cells were first permeatized with saponin at 0.05% (Sigma-Aldrich, Saint Louis, Mo.) in PBS in the blocking stage, and 0.05% saponin/PBS was added in each after the reaction stage. Normal serum was used as first antibody control.

Protein extracts were prepared from Apo-Nec cell lines of the invention. Cell pellets were frozen at −80° C., thawed, and treated for 20 min at 4° C. with lysis buffer (50 mM Tris-ClH, pH 7.5, 1% $NP_40$, 150 mM de NaCl, 5 mM de EDTA, and 1 mM PMSF). The suspension was homogenized with a Polytron (Brinkmann Instruments, USA), and was centrifuged for 40 min at 10,000 g. Supernatant was stored as aliquots frozen at −20° C. Protein concentration was measured according to the Lowry method. IIB-BR-G human breast carcinoma cell line protein extracts were likewise prepared.

Protein extracts (50 μg) were run in a SDS-PAGE 3%-12% gradient, and transferred to a nitro-cellulose membrane (0.45 μm pore, Sigma-Aldrich, Saint Louis, Mo., USA). After blocking with 3% skimmed bovine milk (Moliko, Argentina), they were incubated overnight at 4° C. with patient serum diluted 1/10. After several washings, the membranes were incubated with human anti-IgG+A+M antibodies obtained in goat, conjugated with horseradish peroxidase (HRP) (Zymed, San Francisco, Calif.), and developed with 4-Cl-naphthol plus $H_2O_2$.

Histopathologic Analysis of Melanoma Metastases:

Paraffin-embedded biopsies were used to analyze lymphoid cells, and DCs cell infiltration. Between three and five sections were stained with hematoxylin/eosin, or immunostained with anti-CD4 (1F6 clon), anti-CD8 (C8E—144b clon), anti-CD20 (L26 clon), anti-CD1a (010 clon) (DakoCytomation, Glostrup, DK), and anti-CD57 (NK1 clon, Zymed, San Francisco, Calif.) antibodies, and developed with ABC reactant, and diamino-benzidine (DAB), or Novared as substrate (Vectastain, Vector, Burlingame, Calif.). Reactions were conducted as control by omitting primary antibodies. Sections were analyzed with an Olympus BX40 microscope.

The invention claimed is:

1. A human melanoma cell line for the treatment of malignant diseases characterized by such cell line being selected from the group comprising (a) Mel-XYI (deposited at German Collection of Microorganisms and Cell Cultures DSMZ under access number DSM ACC2830), (b) Mel-XY2 (deposited at German Collection of Microorganisms and Cell Cultures DSMZ under access number DSM ACC2831), (c) Mel-XY3 (deposited at German Collection of Microorganisms and Cell Cultures DSMZ under access number DSM ACC2832), and (d) Mel-XX4 (deposited at German Collection of Microorganisms and Cell Cultures DSMZ under access number DSM ACC2829).

2. The cell line of claim 1, characterized in that the cell line is the cell line Mel-XY1 deposited at German Collection of Microorganisms and under access number DSM ACC2830.

3. The cell line of claim 1, characterized in that the cell line is the cell line Mel-XY2 deposited at German Collection of Microorganisms and under access number DSM ACC2831.

4. The cell line of claim 1, characterized in that the cell line is the cell line Mel-XY3 deposited at German Collection of Microorganisms and under access number DSM ACC2832.

5. The cell line of claim 1, characterized in that the cell line is the cell line Mel-XX4 deposited at German Collection of Microorganisms and Cell Cultures DSMZ under access number DSM ACC2829.

6. A composition for the treatment of melanoma, characterized by comprising at least one allogenic melanoma cell line selected from the group comprising (a) Mel-XYI (deposited at German Collection of Microorganisms and Cell Cultures DSMZ under access number DSM ACC2830), (b) Mel-XY2 (deposited at German Collection of Microorganisms and Cell Cultures DSMZ under access number DSM ACC2831), (c) Mel-XY3 (deposited at German Collection of Microorganisms and Cell Cultures DSMZ under access number DSM ACC2832), (d) Mel-XX4 (deposited at German Collection of Microorganisms and Cell Cultures DSMZ under access number DSM ACC2829), and combinations thereof, where such cell lines have been irradiated, and are incapable of proliferating.

7. The composition of claim 6, characterized by additionally comprising excipients, adjuvants, and immuno-modifiers.

8. The composition of claim 7, characterized in that the adjuvant is BCG.

9. The composition of claim 7, characterized in that the immuno-modifier is selected from the group comprising GM-CSF, G-CSF, IFNa, cyclophosphamide, and mixtures thereof.

10. The composition of claim 6, characterized in that the irradiated cell line comprises an amount from 35% to 60% of apoptotic cells.

11. The composition of claim 6, characterized in that the irradiated cell line comprises an amount from 10% to 25% of necrotic cells.

12. The composition of claim 6, characterized in that it comprises at least one combination of the allogenic melanoma cell lines (a) Mel-XYI (deposited at German Collection of Microorganisms and Cell Cultures DSMZ under access number DSM ACC2830), (b) Mel-XY2 (deposited at German Collection of Microorganisms and Cell Cultures DSMZ under access number DSM ACC2831), (c) Mel-XY3 (deposited at German Collection of Microorganisms and Cell Cultures DSMZ under access number DSM ACC2832), and (d) Mel-XX4 (deposited at German Collection of Microorganisms and Cell Cultures DSMZ under access number DSM ACC2829), where such cell lines have been irradiated, and are incapable of proliferating.

13. The composition of claim 12, characterized in that additionally it comprises excipients, adjuvants, and immunomodifiers.

14. The composition of claim 6, characterized in that it comprises at least one combination of the allogenic melanoma cell lines (a) Mel-XYI (deposited at German Collection of Microorganisms and Cell Cultures DSMZ under access number DSM ACC2830), (b) Mel-XY2 (deposited at German Collection of Microorganisms and Cell Cultures DSMZ under access number DSM ACC2831), and (c) Mel-XY3 (deposited at German Collection of Microorganisms and Cell Cultures DSMZ under access number DSM ACC2832), where such cell lines have been irradiated and are incapable of proliferating.

15. The composition of claim 14, characterized in that it additionally comprises excipients, adjuvants, and immunomodifiers.

16. A composition for the treatment of human melanomas, characterized by comprising mature autologous dendritic cells, autologous dendritic cells charged with a combination of heterologous human melanoma cell line, apoptotic cells from such heterologous human melanoma cell line, and necrotic cells from such heterologous human melanoma cell line, wherein heterologous melanoma cell line is a combination of (a) Mel-XYI (deposited at German Collection of Microorganisms and Cell Cultures DSMZ under access number DSM ACC2830), (b) Mel-XY2 (deposited at German Collection of Microorganisms and Cell Cultures DSMZ under access number DSM ACC2831), (c) Mel-XY3 (deposited at German Collection of Microorganisms and Cell Cultures DSMZ under access number DSM ACC2832), and (d) Mel-XX4 (deposited at German Collection of Microorganisms and Cell Cultures DSMZ under access number DSM ACC2829), where such cell line have been irradiated, and are incapable of proliferating.

17. The composition of claim 16, characterized in that the mature dendritic cells have $CD14^-$, $CDIIc^+$, $CDIa^+$, and $CD83^+$ phenotype.

18. The composition of claim 16, characterized by additionally comprising excipients, adjuvants, and immunomodifiers.

19. A procedure for preparing the composition according to claim 6, characterized by comprising the stages of:
  a) thawing and culturing cell lines selected from the group comprised (a) Mel-XY1 (deposited at German Collection of Microorganisms and Cell Cultures DSMZ under access number DSM ACC2830), (b) Mel-XY2 (deposited at German Collection of Microorganisms and Cell Cultures DSMZ under access number DSM ACC2831), (c) Mel-XY3 (deposited at German Collection of Microorganisms and Cell Cultures DSMZ under access number DSM ACC2832), and Mel-XX4 (deposited at German Collection of Microorganisms and Cell Cultures DSMZ under access number DSM ACC2829);
  b) irradiating such cell lines; and
  c) adding adjuvants and/or excipients.

20. The procedure of claim 19, characterized in that the cells are irradiated at a value from 50 to 100 Gy.

21. The procedure of claim 19, characterized in that the adjuvant is BCG.

22. The procedure of claim 19, characterized in that in stage c) and immuno-modifier selected form the group of GM-CSF, G-CSF, IFNa, cyclophosphamide and mixtures thereof.

23. The procedure of claim 19, characterized in that it comprises a stage of mixing the cell lines.

24. A procedure for preparing the composition according to claim 16, characterized by comprising the stages of:
  a) thawing and culturing cell lines selected from the group comprising (a) Mel-XY1 (deposited at German Collection of Microorganisms and Cell Cultures DSMZ under access number DSM ACC2830), (b) Mel-XY2 (deposited at German Collection of Microorganisms and Cell Cultures DSMZ under access number DSM ACC2831), (c) Mel-XY3 (deposited at German Collection of Microorganisms and Cell Cultures DSMZ under access number DSM ACC2832), and (d) Mel-XX4 (deposited at German Collection of Microorganisms and Cell Cultures DSMZ under access number DSM ACC2829);
  b) irradiating such cell lines;
  c) obtaining autologous dendritic cells, and
  d) co-culturing for a time the autologous dendritic cells irradiated in stage b).

25. The procedure of claim 24, characterized in that the cells are irradiated at a value from 50 to 100 Gy.

26. The procedure of claim 24, characterized in that co-culture is conducted at a temperature from 35 to 39° C., and for a period of time from 6 to 72 hours.

27. The procedure of claim 24, characterized in that in stage d) the relation between autologous dendritic cells, and cell lines is from 1:1 to 3:1.

28. The procedure of claim 24, characterized in that dendritic cells of stage d) comprise immature dendritic cells.

29. The procedure of claim 24, characterized in that the composition comprises a stage of mixing the cell lines.

30. A method for inducing an anti-tumor immune response in patients carrying a melanoma characterized in that it comprises administering to a patient in need thereof an effective amount of a combination of cell lines (a) Mel-XYI (deposited at German Collection of Microorganisms and Cell Cultures DSMZ under access number DSM ACC2830), (b) Mel-XY2 (deposited at German Collection of Microorganisms and Cell Cultures DSMZ under access number DSM ACC2831), and (c) Mel-XY3 (deposited at German Collection of Microorganisms and Cell Cultures DSMZ under access number DSM ACC2832), where such cell lines are incapable of proliferating.

31. The treatment method of claim 30, characterized in that the combination of cell lines is administered together with an adjuvant.

32. The treatment method of claim 31, characterized in that the adjuvant is BCG in an amount from 0.1 to $2 \times 10^6$ colony forming units per application dose.

33. The treatment method of claim 30, characterized in that the combination of cell lines is administered together with an immunomodulator.

34. The treatment method of claim 33, characterized in that the immunomodulator is GM-CSF in an amount from 100 to 600 mg per application dose.

35. The treatment method of claim 30, characterized in that the effective amount of cells comprises between 5 and $50 \times 106$ of the cell combination.

36. A method for inducing an anti-tumor immune response in patients carrying a melanoma characterized comprising administering to a patient in need thereof an effective amount of a combination of cell lines (a) Mel-XV1 (deposited at German Collection of Microorganisms and Cell Cultures DSMZ under access number DSM ACC2830), (b) Mel-XY2 (deposited at German Collection of Microorganisms and Cell Cultures DSMZ under access number DSM ACC2831), (c) Mel-XY3 (deposited at German Collection of Microorganisms and Cell Cultures DSMZ under access number DSM ACC2832), and (d) Mel-XX4 (deposited at German Collection of Microorganisms and Cell Cultures DSMZ under access number DSM ACC2829), where such cell lines are incapable of proliferating.

37. The treatment method of claim 36, characterized in that the combination of cell lines is administered together with an adjuvant.

38. The treatment method of claim 37, characterized in that the adjuvant is BCG in an amount from 0.1 to $2 \times 10^6$ colony forming units per application dose.

39. The treatment method of claim 36, characterized in that the combination of cell lines is administered together with an immunomodulator.

40. The treatment method of claim 39, characterized in that the immunomodulator is GM-CSF in an amount from 100 to 600 mg per application dose.

41. The treatment method of claim 36, characterized in that the effective amount of cells comprises from 5 to $50 \times 10^6$ cell combination.

42. A method for inducing an anti-tumor immune response in patients carrying a melanoma characterized in that it comprises administering to a patient in need thereof an effective amount of a co-culture from 6 to 72 hours of autologous dendritic cells, and a combination of cell lines (a) Mel-XYI (deposited at German Collection of Microorganisms and Cell Cultures DSMZ under access number DSM ACC2830), (b) Mel-XY2 (deposited at German Collection of Microorganisms and Cell Cultures DSMZ under access number DSM ACC2831), (c) Mel-XY3 (deposited at German Collection of Microorganisms and Cell Cultures DSMZ under access number DSM ACC2832), and (d) Mel-XX4 (deposited at German Collection of Microorganisms and Cell Cultures DSMZ under access number DSM ACC2829), where such cell lines are incapable of proliferating.

43. The method of claim 42, characterized in that the autologous dendritic cells at the beginning of the co-culture are immature dendritic cells, and al the end of the co-culture are a mixture of mature autologous dendritic cells, and autologous dendritic cells charged with cell lines (a) Mel-XY1 (deposited at German Collection of Microorganisms and Cell Cultures DSMZ under access number DSM ACC2830), (b) Mel-XY2 (deposited at German Collection of Microorganisms and Cell Cultures DSMZ under access number DSM ACC2831), (c) Mel-XY3 (deposited at German Collection of Microorganisms and Cell Cultures DSMZ under access number DSM ACC2832), and (d) Mel-XX4 (deposited at German Collection of Microorganisms and Cell Cultures DSMZ under access number DSM ACC2829).

44. The method of claim 42, characterized in that at the end of the co-culture the cells of each cell line comprise a mixture of apoptotic cell populations, and necrotic cell populations.

45. The method of claim 42, characterized in that the effective amount of cells from the cc-culture comprise from 5 to $50 \times 10^6$ total cells.

* * * * *